US008497306B2

(12) United States Patent
Sielecki-Dzurdz

(10) Patent No.: US 8,497,306 B2
(45) Date of Patent: Jul. 30, 2013

(54) GUANYLHYDRAZONE SALTS, COMPOSITIONS, PROCESSES OF MAKING, AND METHODS OF USING

(75) Inventor: Thais M. Sielecki-Dzurdz, Kennett Square, PA (US)

(73) Assignee: Ferring B.V., Hoofddorp (NL)

( * ) Notice: Subject to any disclaimer, the term of this patent is extended or adjusted under 35 U.S.C. 154(b) by 1085 days.

(21) Appl. No.: 11/931,738

(22) Filed: Oct. 31, 2007

(65) Prior Publication Data

US 2008/0262090 A1 Oct. 23, 2008

Related U.S. Application Data

(63) Continuation of application No. 11/766,794, filed on Jun. 22, 2007, which is a continuation of application No. 11/165,255, filed on Jun. 24, 2005, now Pat. No. 7,244,765.

(60) Provisional application No. 60/582,532, filed on Jun. 25, 2004, provisional application No. 60/601,992, filed on Aug. 17, 2004.

(51) Int. Cl.
*A01N 37/52* (2006.01)

(52) U.S. Cl.
USPC ............ 514/632; 514/597; 564/152; 564/228

(58) Field of Classification Search
None
See application file for complete search history.

(56) References Cited

U.S. PATENT DOCUMENTS

| | | | |
|---|---|---|---|
| 4,321,253 A | 3/1982 | Beatty | |
| 4,482,722 A | 11/1984 | Thorbek et al. | |
| 4,572,909 A | 2/1986 | Campbell et al. | |
| 4,704,397 A | 11/1987 | Fisher et al. | |
| 4,791,196 A | 12/1988 | Ide et al. | |
| 5,028,625 A | 7/1991 | Motola et al. | |
| 5,272,165 A * | 12/1993 | Ulrich et al. | 514/357 |
| 5,599,984 A * | 2/1997 | Bianchi et al. | 564/157 |
| 5,690,954 A | 11/1997 | Illum | |
| 5,750,573 A | 5/1998 | Bianchi et al. | |
| 5,753,684 A | 5/1998 | Bianchi et al. | |
| 5,849,794 A | 12/1998 | Bianchi et al. | |
| 5,854,289 A | 12/1998 | Bianchi et al. | |
| 5,859,062 A | 1/1999 | Bianchi et al. | |
| 5,980,952 A | 11/1999 | De Barochez et al. | |
| 5,993,858 A | 11/1999 | Crison et al. | |
| 6,008,255 A | 12/1999 | Bianchi et al. | |
| 6,022,900 A | 2/2000 | Bianchi et al. | |
| 6,028,054 A | 2/2000 | Benet et al. | |
| 6,143,728 A * | 11/2000 | Tracey et al. | 514/44 R |
| 6,180,676 B1 * | 1/2001 | Bianchi et al. | 514/597 |
| 6,248,787 B1 | 6/2001 | Bianchi et al. | |
| 6,255,502 B1 | 7/2001 | Penkler et al. | |
| 6,277,405 B1 | 8/2001 | Stamm et al. | |
| 6,319,894 B1 | 11/2001 | Tracey et al. | |
| 6,576,651 B2 | 6/2003 | Bandyopadhyay et al. | |
| 6,673,777 B1 | 1/2004 | Tracey et al. | |
| 6,689,777 B2 | 2/2004 | Ulrich et al. | |
| 7,244,765 B2 * | 7/2007 | Sielecki-Dzurdz | 514/554 |
| 7,741,372 B2 * | 6/2010 | Tracey et al. | 514/632 |
| 2002/0028851 A1 | 3/2002 | Bianchi et al. | |
| 2003/0040464 A1 | 2/2003 | Wong et al. | |
| 2003/0096761 A1 | 5/2003 | Burnside et al. | |
| 2003/0134904 A1 | 7/2003 | Giordano et al. | |
| 2003/0139446 A1 | 7/2003 | Chen et al. | |
| 2003/0144510 A1 | 7/2003 | Gala et al. | |
| 2003/0181487 A1 | 9/2003 | Kamiyama et al. | |
| 2003/0191176 A1 | 10/2003 | Dunn et al. | |
| 2003/0198669 A1 | 10/2003 | Cutler et al. | |
| 2003/0203969 A1 | 10/2003 | Bevec et al. | |
| 2004/0043079 A1 | 3/2004 | D'Souza | |
| 2008/0146670 A1 * | 6/2008 | Sielecki-Dzurdz | 514/615 |

OTHER PUBLICATIONS

Tong et al., {In Situ Salt Screening—A useful Technique for Discovery Support and Performance Studies}, Pharmaceutical Development and Technology, 3(2), 215-223, (1998)}.*
Engel et al., {Salt form Selection and Characterization of LY333531 Mesylate Monohydrate, International Journal of Pharmaceutics 198, 2000, 239-247}.*
Berge et al., {Journal of Pharmaceutical Sciences, Pharmaceutical Salts, vol. 66, 1,Jan. 1977, 1-19}.*
Magali Sautel, Patrick Dorion, Benoit Robert, My Truong. Salt and Polymorph Selection: Fundamental Topics in any Pharmaceutical Development. Analytical Sciences Department, Longjumeau, France, Jul. 12, 2003.
M.J. D'Souza, C.W. Oettinger, G.V. Milton, K.J. Tracey. Prevention of Lethality and Suppression of Proinflammatory Cytokines in Experimental Septic Shock by Microencapsulated CNI-1493. Journal of Interferon and Cytokine Research, 1999, 19:1125-1133.
Marc Stranz, Eric S. Kastango, A Review of pH and Osmolarity. International Journal of Pharmaceutical Compounding, vol. 6 No. 3, 216-220, May/Jun. 2002.
Gary L. Engel, Nagy A. Farid, Margaret M. Faul, Lori A. Richardson, Leonard L. Winneroski, Salt form selection and characterization of LY333531 mesylate monohydrate. International Journal of Pharmaceutics 198 (2000):239-247.
Emily C. Ware, D. Robert Lu, An automated approach to salt selection for new unique trazodone salts. Pharmaceutical Research, Jan. 2004, vol. 21(1):177-184.
Wei-Qin (Tony) Tong, Graham Whitesell, In situ salt screening—a useful technique for discovery support and preformulation studies. Pharmaceutical Development and Technology 3(2),215-223 (1998).
Abu T. M. Serajuddin, Pai-Chang Sheen, Daniel Mufson, David F. Bernstein, Matthew A. Augustine . Preformulation study of a poorly water-soluble drug, alpha-Pentyl-3-(2-quinolinylmethoxy) benzenemethanol: Selection of the base for dosage form design. J. Pharm. Sci. May 1986;75(5):492-496.
Lian-Feng Huang, Wei-Qin (Tony) Tong, Impact of solid state properties on developability assessment of drug candidates. Advanced Drug Delivery Reviews 56 (2004) 321-334.
PCT/US05/22626, International Search Report, dated Feb. 21, 2006.
PCT/US05/22626, Written Opinion of the International Searching Authority, dated Feb. 21, 2006.

* cited by examiner

*Primary Examiner* — Sudhakar Katakam
(74) *Attorney, Agent, or Firm* — Fish & Richardson P.C.

(57) ABSTRACT

The invention relates to pharmaceutically acceptable salts of guanylhydrazone-containing compounds, for example, Semapimod. The invention also relates to pharmaceutically acceptable compositions comprising the salts and methods for their use.

14 Claims, No Drawings

GUANYLHYDRAZONE SALTS, COMPOSITIONS, PROCESSES OF MAKING, AND METHODS OF USING

CROSS-REFERENCE TO RELATED APPLICATIONS

This application claims priority to U.S. Provisional Application Ser. Nos. 60/582,532, filed Jun. 25, 2004, and 60/601,992, filed Aug. 17, 2004, the entire contents of each of which are hereby incorporated by reference.

BACKGROUND OF THE INVENTION

1. Field of the Invention

The present invention is directed to the field of pharmacology. In one aspect, the invention is directed to improved salts of guanylhydrazone compounds. In another aspect, the invention is directed to the formulation of pharmaceutical compositions containing improved salts of guanylhydrazone compounds. The guanylhydrazone salts may be used for preventive or therapeutic regimens or for the identification of candidate compounds for producing effective drugs having increased or modulated solubility in water or a neutral solution for enhancing or modulating bioavailability.

2. Related Art

United States Patent Application Publication No. 2004/0043079 to D'Souza relates to microencapsulation as a delivery vehicle for a drug. The guanylhydrazone compound Semapimod is disclosed in one embodiment.

United States Patent Application Publication No. 2003/0134904 to Giordano et al. relates to guanylhydrazone compounds for inhibiting RNase P activity.

United States Patent Application Publication No. 2003/0203969 to Bevec et al. relates to pharmaceutically active aromatic guanylhydrazone compounds.

United States Patent Application Publication No. 2002/0028851 to Bianchi et al. relates to guanylhydrazone compounds and their uses to treat inflammatory conditions.

U.S. Pat. Nos. 6,673,777 and 6,143,728 to Tracey et al. relate to guanylhydrazone compounds and their uses for treating diseases associated with T cell activation.

U.S. Pat. Nos. 6,248,787; 6,180,676; 6,022,900; 6,008,255; 5,859,062; 5,854,289; 5,849,794; 5,753,684; 5,750,573; and 5,599,984 all to Bianchi et al. relate to guanylhydrazone compounds and their uses to treat inflammatory conditions.

All references cited herein are incorporated by reference for all purposes.

BACKGROUND OF THE TECHNOLOGY

Solubility in solution, either for a drug compound with a recognized activity or for a drug candidate compound, is almost always required before the compound can be analyzed or significant bioavailability achieved. Solubility in water or some aqueous or neutral solution is desirable as high solubility eases molecular pharmacology screening as well as biodistribution.

In vitro studies involving such aspects as receptor binding, enzyme inhibition, and cell cultures and studies with isolated organs are all facilitated when the compound is made soluble in $H_2O$ or other neutral media. When testing highly water insoluble material for in vitro assays, the common procedure to attain water solubility is to prepare a solution using an organic solvent (DMSO, polyethylene glycol, EtOH, etc.) and then proceed to various aqueous dilutions. In following this regimen, there is always the possibility that the compound will precipitate out during a dilution. Furthermore, any precipitation may not be properly considered if it is not noticeable or the precipitate easily adheres to the wall of the testing vessel.

Most organic acids or bases are only poorly soluble in water, whereas many corresponding salts render the drug substance ionized in $H_2O$ and hence made water soluble. Salts that are soluble in water are also ideally suited for the preparation of injectable sterile aqueous solutions. Also, fast dissolution of the active principle contained in solid dosage forms, such as for quick release tablets or hard-gelatine capsules will rely on the aqueous solubility of the drug.

When considering in vivo testing, solubility in $H_2O$ facilitates all studies in which parenteral administration is required. In pharmacokinetics, a reliable determination of absolute bioavailability via oral administration is needed before a comparison is possible with an amount administered intravenously because a dose entering the system by the parenteral route is a precisely known reference. Aqueous solubility is particularly important in toxicity studies wherein the digestibility of a compound in an animal will leave uncertainty as to whether an insoluble compound is either toxic or just incompletely absorbed.

On a therapeutic level, the major concern for finding a water-soluble drug resides in the possibility this solubility provides for intravenous administration. The water solubility of a drug is particularly important in drugs for emergency treatments that will permit therapeutic plasma levels to be reached in a very short period of time. Intravenous administration is often the only access available when a patient is otherwise incapacitated in an operation or some emergency situation. Also, water solubility is needed for several types of pharmaceutical dosage formats. Apart from parenteral injection or infusion, water solubility is important for producing aqueous drops for ocular or nasal administration, or aqueous syrup for oral administration.

For oral consumption of a drug compound, the significance of water solubility to pharmacokinetics cannot be underestimated. This is particularly so when the absorption step for the compound is preceded by a dissolution step of the orally ingested dosage format. The in-vivo dissolution step is often the rate determining step for drug absorption. Also, highly water-soluble drugs are, by the fact itself, less toxic than lower water-soluble drugs due to their facilitated renal clearance. They will have a lesser tendency to accumulate in an organism thus avoiding overload to the liver.

Complex guanylhydrazones have been reported in the patent literature above. For instance, U.S. Pat. No. 5,599,984 to Bianchi et al. listed above discloses hydrochloride salts of complex guanylhydrazone compounds with some degree of water solubility. However, the high acidity associated with some hydrochloride salts, upon dissociation, can cause cellular damage and is a recognized source of phlebitis. Stranz et al., *Int. J. Pharm. Compounding* (2002), v. 6, n. 3, pp. 216-220. Thus, there is a need in the art to develop salts of guanylhydrazone compounds, and in particular salts of complex guanylhydrazone compounds, having both high water solubility and lower probability of cellular insult due to the acidity of the salt upon dissociation in solution.

SUMMARY OF THE INVENTION

One embodiment of the present invention provides a pharmaceutically acceptable salt, comprising the following compound:

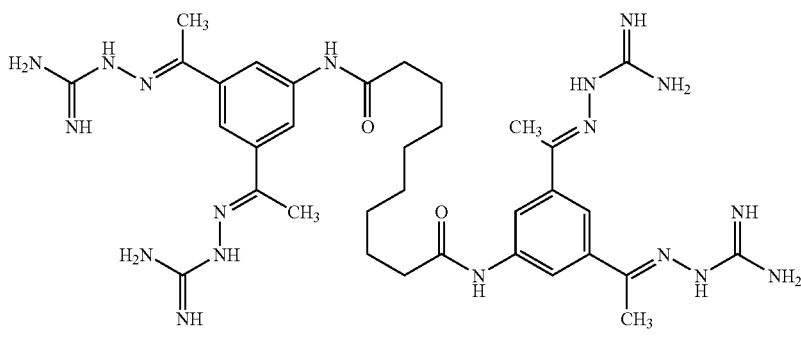

CNI-1493 as a salt of at least one pharmaceutically acceptable acid selected from the group consisting of compounds having the following formulas:

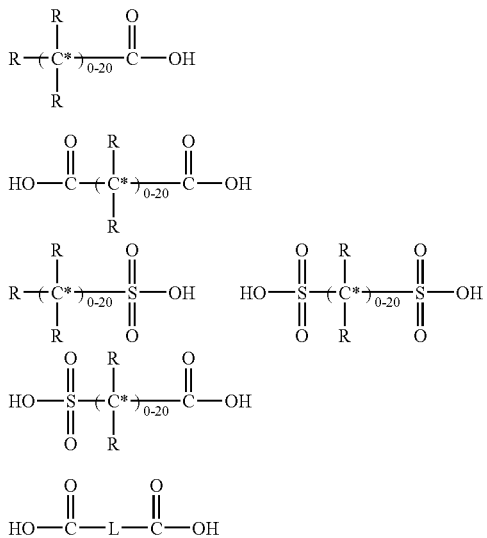

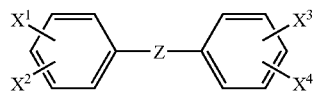

wherein each C* independently represents a potentially chiral carbon that can be in either the D or L enantiomeric configuration, wherein each R is independently unsubstituted or substituted and selected from the group consisting of Y—, Y—O—, Y—S—, Y—SO$_2$—, (Y)$_2$—N—SO$_2$—, Y—(C=O)—, Y—(C=O)—O—, YO—(C=O)—, (Y)$_2$—N—, Y—(C=O)—(Y—N)—, (Y—(C=O))$_2$—N—, Y—(SO$_2$)—(Y—N)—, or (Y—(SO$_2$))$_2$—N—; each Y being independently selected from the group consisting of hydrogen, carboxyl, halo, hydroxyl, thiol, nitro, amine, NC—, (C$_1$-C$_6$)alkyl, (C$_3$-C$_6$)cycloalkyl, (C$_2$-C$_6$)alkenyl, (C$_3$-C$_6$)cycloalkenyl, (C$_2$-C$_6$)alkynyl, (C$_3$-C$_6$)cycloalkynyl, (C$_1$-C$_6$)alkoxy, (C$_5$-C$_7$)aryl, (C$_3$-C$_5$)heteroaryl, and (C$_3$-C$_5$)heterocyclic; wherein each of the aforesaid (C$_1$-C$_6$)alkyl, (C$_3$-C$_6$)cycloalkyl, (C$_2$-C$_6$)alkenyl, (C$_3$-C$_6$)cycloalkenyl, (C$_2$-C$_6$)alkynyl, (C$_3$-C$_6$)cycloalkynyl, (C$_1$-C$_6$)alkoxy, (C$_5$-C$_7$)aryl, (C$_3$-C$_5$)heteroaryl, and (C$_3$-C$_5$)heterocyclic substituents may be substituted or unsubstituted;

wherein two independently chosen Y alkyl-containing groups may be taken together with any nitrogen atom to which they are attached to form a three to twelve membered cyclic, heterocyclic or heteroaryl ring;

and wherein in the compound having the formula VII, L is a diradical moiety selected from the group consisting of (C$_1$-C$_{20}$)alkyl, (C$_3$-C$_{20}$)cycloalkyl, (C$_2$-C$_{20}$)alkenyl, (C$_3$-C$_{20}$)cycloalkenyl, (C$_2$-C$_{20}$)alkynyl, (C$_3$-C$_{20}$)cycloalkynyl, (C$_1$-C$_{20}$)alkoxy/thiol, (C$_3$-C$_{20}$)aryl, (C$_3$-C$_{15}$)heteroaryl, (C$_3$-C$_{15}$)heterocyclic and (C$_3$-C$_{20}$)cycloalkyl; wherein each of the aforesaid (C$_1$-C$_{20}$)alkyl, (C$_3$-C$_{20}$)cycloalkyl, (C$_2$-C$_{20}$)alkenyl, (C$_3$-C$_{20}$)cycloalkenyl, (C$_2$-C$_{20}$)alkynyl, (C$_3$-C$_{20}$)cycloalkynyl, (C$_1$-C$_{20}$)alkoxy/thiol, (C$_3$-C$_{20}$)aryl, (C$_3$-C$_{15}$)heteroaryl, (C$_3$-C$_{15}$)heterocyclic and (C$_3$-C$_{20}$)cycloalkyl diradical moieties may be substituted or unsubstituted.

Another embodiment of the invention provides a pharmaceutically acceptable salt, comprising one or more compounds having the formula:

$$X^1 \diagdown \diagup Z \diagdown \diagup X^3$$
$$X^2 \diagup \qquad \diagup X^4$$

wherein $X^1$, $X^2$, $X^3$, and $X^4$ each independently represent H, GhyCH—, GhyCCH$_3$—, or CH$_3$CO—, with the provisos that $X^1$, $X^2$, $X^3$ and $X^4$ are not simultaneously H;

wherein Z is one or more selected from the group consisting of:

-(A$^1$)$_a$-(CR$^2$R$^3$)$_x$-(A$^2$)$_b$-;
-(A$^1$)$_a$-(CR$^2$R$^3$)$_x$-Q$_m$-(CR$^4$R$^5$)$_y$-(A$^2$)$_b$-; and
-(A$^1$)$_a$-(CR$^2$R$^3$)$_x$-Q$_m$-(CR$^4$R$^5$)$_y$-T$_n$-(CR$^6$R$^7$)$_z$-(A$^2$)$_b$-;
and combinations thereof;

wherein a is selected from the group consisting of 0, 1, 2, 3, 4, 5, 6, 7, 8, and 9;

wherein b is selected from the group consisting of 0, 1, 2, 3, 4, 5, 6, 7, 8, and 9;

wherein x is selected from the group consisting of 0, 1, 2, 3, 4, 5, 6, 7, 8, and 9;

wherein y is selected from the group consisting of 0, 1, 2, 3, 4, 5, 6, 7, 8, and 9;

wherein z is selected from the group consisting of 0, 1, 2, 3, 4, 5, 6, 7, 8, and 9;

wherein m is selected from the group consisting of 0, 1, 2, 3, 4, 5, 6, 7, 8, and 9;

wherein n is selected from the group consisting of 0, 1, 2, 3, 4, 5, 6, 7, 8, and 9;

wherein A$^1$ and A$^2$ are each independently selected from the group consisting of —NR$^8$(CO)NR$^9$—, —(CO)NR$^8$, —NR$^8$(CO)—, —NR$^8$—, —O—, —S—, —S(=O)—, —SO$_2$—, —SO$_2$NR$^8$—, —NR$^8$SO$_2$—, and salts thereof;

wherein Q and T are each independently selected from the group consisting of —NR$^{10}$(CO)NR$^{11}$—, —(CO)NR$^{10}$—, —$NR^{10}$(CO)—, —$NR^{10}$—, —O—, —S—, —S(=O)—, —$SO_2$—, —$SO_2NR^{10}$—, —$NR^{10}SO_2$—, salts thereof, branched or unbranched, saturated or unsaturated, substituted or unsubstituted $C_1$-$C_{20}$ alkylene, saturated or unsaturated, substituted or unsubstituted $C_3$-$C_{20}$ cycloalkylene, substituted or unsubstituted $C_5$-$C_{25}$ arylene, and combinations thereof;

wherein one or more carbon atoms in any of said alkylene, cycloalkylene or arylene in said Q and/or T may each be independently replaced with one or more heteroatoms selected from the group consisting of nitrogen, oxygen, sulfur, and a combination thereof;

and wherein when substituted, said alkylene, cycloalkylene or arylene in said Q and/or T are each independently substituted with one or more substituent groups selected from the group consisting of hydroxy, halo, bromo, chloro, iodo, fluoro, —$N_3$, —CN, —NC, —SH, —$NO_2$, —$NH_2$, ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$)cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, ($C_2$-$C_{20}$)alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2N$—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O){(($C_1$-$C_{20}$)alkyl)N}—, ($C_1$-$C_{20}$)alkoxy-(C=O)—{(($C_1$-$C_{20}$)alkyl)N}—, ($C_3$-$C_{25}$)heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$) cycloalkenyl-C=O)—{(($C_1$-$C_{20}$)alkyl)N}—, ($C_2$-$C_{20}$)alkynyl-(C=O){(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O)—{(($C_1$-$C_{20}$)alkyl)N}—, phenyl-(C=O)—NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, $H_2N$(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—C=O)—, {($C_2$-$C_{20}$)alkenyl}{phenyl}N—C=O)—, {($C_3$-$C_{20}$)cycloalkenyl}{phenyl}N—C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O#, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—

O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-C_{20})$cycloalkenyl-(C=O)—O—, $(C_2-C_{20})$alkynyl-(C=O)—O—, $(C_5-C_{25})$aryl-(C=O)—O—, phenyl-(C=O)—O—, perhalo$(C_1-C_{20})$alkyl-(C=O)—O—, and salts thereof;

wherein each of the aforesaid $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, and $(C_5-C_{25})$aryl groups (as substituents on said alkylene, cycloalkylene or arylene of said Q and T) may be optionally and independently substituted by one to four moieties selected from the group consisting of hydroxy, halo, bromo, chloro, iodo, fluoro, —N$_3$, —CN, —NC, —SH, —NO$_2$, —NH$_2$, $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, $(C_5-C_{25})$aryl, perhalo$(C_1-C_{20})$alkyl, $(C_1-C_{20})$alkyl-O—, phenyl-O—, $(C_3-C_{20})$cycloalkyl-O—, $(C_3-C_{25})$heteroaryl-O—, $(C_3-C_{25})$heterocyclic-O—, $(C_2-C_{20})$alkenyl-O—, $(C_3-C_{20})$cycloalkenyl-O—, $(C_2-C_{20})$alkynyl-O—, $(C_5-C_{20})$cycloalkynyl-O—, $(C_5-C_{25})$aryl-O—, perhalo$(C_1-C_{20})$alkyl-O—, $(C_1-C_{20})$alkyl-S—, phenyl-S—, $(C_3-C_{20})$cycloalkyl-S—, $(C_3-C_{25})$heteroaryl-S—, $(C_3-C_{25})$heterocyclic-S—, $(C_2-C_{20})$alkenyl-S—, $(C_3-C_{20})$cycloalkenyl-S—, $(C_2-C_{20})$alkynyl-S—, $(C_5-C_{20})$cycloalkynyl-S—, $(C_5-C_{25})$aryl-S—, perhalo$(C_1-C_{20})$alkyl-S—, $(C_1-C_{20})$alkyl-SO$_2$—, phenyl-SO$_2$—, $(C_3-C_{20})$cycloalkyl-SO$_2$—, $(C_1-C_{20})$alkoxy-SO$_2$—, $(C_3-C_{25})$heteroaryl-SO$_2$—, $(C_3-C_{25})$heterocyclic-SO$_2$—, $(C_2-C_{20})$alkenyl-SO$_2$—, $(C_3-C_{20})$cycloalkenyl-SO$_2$—, $(C_2-C_{20})$alkynyl-SO$_2$—, $(C_5-C_{20})$cycloalkynyl-SO$_2$—, $(C_5-C_{25})$aryl-SO$_2$—, perhalo$(C_1-C_{20})$alkyl-SO$_2$—, H$_2$N—SO$_2$—, $(C_1-C_{20})$alkyl-NH—SO$_2$—, phenyl-NH—SO$_2$—, $(C_3-C_{20})$cycloalkyl-NH—SO$_2$—, $(C_1-C_{20})$alkoxy-NH—SO$_2$—, $(C_3-C_{25})$heteroaryl-NH—SO$_2$—, $(C_3-C_{25})$heterocyclic-NH—SO$_2$—, $(C_2-C_{20})$alkenyl-NH—SO$_2$—, $(C_3-C_{20})$cycloalkenyl-NH—SO$_2$—, $(C_2-C_{20})$alkynyl-NH—SO$_2$—, $(C_5-C_{20})$cycloalkynyl-NH—SO$_2$—, $(C_5-C_{25})$aryl-NH—SO$_2$—, perhalo$(C_1-C_{20})$alkyl-NH—SO$_2$—, {$(C_1-C_{20})$alkyl}$_2$N—SO$_2$—, {phenyl}$_2$N—SO$_2$—, {$(C_3-C_{20})$cycloalkyl}$_2$N—SO$_2$—, {$(C_1-C_{20})$alkoxy}$_2$N—SO$_2$—, {$(C_3-C_{25})$heteroaryl}$_2$N—SO$_2$—, {$(C_3-C_{25})$heterocyclic}$_2$N—SO$_2$—, {$(C_2-C_{20})$alkenyl}$_2$N—SO$_2$—, {$(C_2-C_{20})$alkynyl}$_2$N—SO$_2$—, {$(C_5-C_{20})$cycloalkynyl}$_2$N—SO$_2$—, {$(C_5-C_{25})$aryl}$_2$N—SO$_2$—, {perhalo$(C_1-C_{20})$alkyl}$_2$N—SO$_2$—, $(C_1-C_{20})$alkyl-SO$_2$—NH—, phenyl-SO$_2$—NH—, $(C_3-C_{20})$cycloalkyl-SO$_2$—NH—, $(C_1-C_{20})$alkoxy-SO$_2$—NH—, $(C_3-C_{25})$heteroaryl-SO$_2$—NH—, $(C_3-C_{25})$heterocyclic-SO$_2$—NH—, $(C_2-C_{20})$alkenyl-SO$_2$—NH—, $(C_3-C_{20})$cycloalkenyl-SO$_2$—NH—, $(C_2-C_{20})$alkynyl-SO$_2$—NH—, $(C_5-C_{20})$cycloalkynyl-SO$_2$—NH—, $(C_5-C_{25})$aryl-SO$_2$—NH—, perhalo$(C_1-C_{20})$alkyl-SO$_2$—NH—, $(C_1-C_{20})$alkyl-NH—, phenyl-NH—, $(C_3-C_{20})$cycloalkyl-NH—, $(C_1-C_{20})$alkoxy-NH—, $(C_3-C_{25})$heteroaryl-NH—, $(C_3-C_{25})$heterocyclic-NH—, $(C_2-C_{20})$alkenyl-NH—, $(C_3-C_{20})$cycloalkenyl-NH—, $(C_2-C_{20})$alkynyl-NH—, $(C_5-C_{20})$cycloalkynyl-NH—, $(C_5-C_{25})$aryl-NH—, perhalo$(C_1-C_{20})$alkyl-NH—, {$(C_1-C_{20})$alkyl}$_2$N—, {phenyl}$_2$N—, {$(C_3-C_{20})$cycloalkyl}$_2$N—, {$(C_1-C_{20})$alkoxy}$_2$N—, {$(C_3-C_{25})$heteroaryl}$_2$N—, {$(C_3-C_{25})$heterocyclic}$_2$N—, {$(C_2-C_{20})$alkenyl}$_2$N—, {$(C_3-C_{20})$cycloalkenyl}$_2$N—, {$(C_2-C_{20})$alkynyl}$_2$N—, {$(C_5-C_{20})$cycloalkynyl}$_2$N—, {$(C_5-C_{25})$aryl}$_2$N—, {perhalo$(C_1-C_{20})$alkyl}$_2$N—, $(C_1-C_{20})$alkyl-(C=O)—NH—, phenyl-(C=O)—NH—, $(C_3-C_{20})$cycloalkyl-(C=O)—NH—, $(C_1-C_{20})$alkoxy-(C=O)—NH—, $(C_3-C_{25})$heteroaryl-(C=O)—NH—, $(C_3-C_{25})$heterocyclic-(C=O)—NH—, $(C_2-C_{20})$alkenyl-(C=O)—NH—, $(C_3-C_{20})$cycloalkenyl-(C=O)—NH—, $(C_2-C_{20})$alkynyl-(C=O)—NH—, $(C_5-C_{20})$cycloalkynyl-(C=O)—NH—, $(C_5-C_{25})$aryl-(C=O)—NH—, perhalo$(C_1-C_{20})$alkyl-(C=O)—NH—, $(C_1-C_{20})$alkyl-(C=O)—{$((C_1-C_{20})$alkyl)N}—, phenyl-(C=O)—{$((C_1-C_{20})$alkyl)N}—, $(C_3-C_{20})$cycloalkyl-(C=O)—{$((C_1-C_{20})$alkyl)N}—, $(C_1-C_{20})$alkoxy-(C=O)—{$((C_1-C_{20})$alkyl)N}—, $(C_3-C_{25})$heteroaryl-(C=O)—{$((C_1-C_{20})$alkyl)N}—, $(C_3-C_{25})$heterocyclic-(C=O)—{$((C_1-C_{20})$alkyl)N}—, $(C_2-C_{20})$alkenyl-(C=O){$((C_1-C_{20})$alkyl)N}—, $(C_3-C_{20})$cycloalkenyl-(C=O)—{$((C_1-C_{20})$alkyl)N}—, $(C_2-C_{20})$alkynyl-(C=O)—{$((C_1-C_{20})$alkyl)N}—, $(C_5-C_{20})$cycloalkynyl-(C=O)—{$((C_1-C_{20})$alkyl)N}—, $(C_5-C_{25})$aryl-(C=O)—{$((C_1-C_{20})$alkyl)N}—, perhalo$(C_1-C_{20})$alkyl-(C=O)—{$((C_1-C_{20})$alkyl)N}—, phenyl-(C=O)—NH—, phenyl-(C=O)-{(phenyl)N}—, $(C_1-C_{20})$alkyl-(C=O)-{(phenyl)N}—, $(C_3-C_{20})$cycloalkyl-(C=O)-{(phenyl)N}—, $(C_1-C_{20})$alkoxy-(C=O)-{(phenyl)N}—, $(C_3-C_{25})$heteroaryl-(C=O)-{(phenyl)N}—, $(C_3-C_{25})$heterocyclic-(C=O)-{(phenyl)N}—, $(C_2-C_{20})$alkenyl-(C=O)-{(phenyl)N}—, $(C_3-C_{20})$cycloalkenyl-(C=O)-{(phenyl)N}—, $(C_2-C_{20})$alkynyl-(C=O)-{(phenyl)N}—, $(C_5-C_{20})$cycloalkynyl-(C=O)-{(phenyl)N}—, $(C_5-C_{25})$aryl-(C=O)-{(phenyl)N}—, perhalo$(C_1-C_{20})$alkyl-(C=O)-{(phenyl)N}—, H$_2$N(C=O)—, $(C_1-C_{20})$alkyl-NH—(C=O)—, phenyl-NH—(C=O)—, $(C_3-C_{20})$cycloalkyl-NH—(C=O)—, $(C_1-C_{20})$alkoxy-NH—(C=O)—, $(C_3-C_{25})$heteroaryl-NH—(C=O)—, $(C_3-C_{25})$heterocyclic-NH—(C=O)—, $(C_2-C_{20})$alkenyl-NH—(C=O)—, $(C_3-C_{20})$cycloalkenyl-NH—(C=O)—, $(C_2-C_{20})$alkynyl-NH—(C=O)—, $(C_5-C_{20})$cycloalkynyl-NH—(C=O)—, $(C_5-C_{25})$aryl-NH—(C=O)—, perhalo$(C_1-C_{20})$alkyl-NH—(C=O)—, {$(C_1-C_{20})$alkyl}$_2$N—(C=O)—, {phenyl}{$(C_1-C_{20})$alkyl}N—(C=O)—, {$(C_3-C_{20})$cycloalkyl}{$(C_1-C_{20})$alkyl}N—(C=O)—, {$(C_1-C_{20})$alkoxy}{$(C_1-C_{20})$alkyl}N—(C=O)—, {$(C_3-C_{25})$heteroaryl}{$(C_1-C_{20})$alkyl}N—(C=O)—, {$(C_3-C_{25})$heterocyclic}{$(C_1-C_{20})$alkyl}N—(C=O)—, {$(C_2-C_{20})$alkenyl}{$(C_1-C_{20})$alkyl}N—(C=O)—, {$(C_3-C_{20})$cycloalkenyl}{$(C_1-C_{20})$alkyl}N—(C=O)—, {$(C_2-C_{20})$alkynyl}{$(C_1-C_{20})$alkyl}N—(C=O)—, {$(C_5-C_{20})$cycloalkynyl}{$(C_1-C_{20})$alkyl}N—(C=O)—, {$(C_5-C_{25})$aryl}{$(C_1-C_{20})$alkyl}N—(C=O)—, {perhalo$(C_1-C_{20})$alkyl}{$(C_1-C_{20})$alkyl}N—(C=O)—, {phenyl}$_2$N—(C=O)—, {$(C_3-C_{20})$cycloalkyl}{phenyl}N—(C=O)—, {$(C_1-C_{20})$alkoxy}{phenyl}N—(C=O)—, {$(C_3-C_{25})$heteroaryl}{phenyl}N—(C=O)—, {$(C_3-C_{25})$heterocyclic}{phenyl}N—(C=O)—, {$(C_2-C_{20})$alkenyl}{phenyl}N—(C=O)—, {$(C_3-C_{20})$cycloalkenyl}{phenyl}N—(C=O)—, {$(C_2-C_{20})$alkynyl}{phenyl}N—(C=O)—, {$(C_5-C_{20})$cycloalkynyl}{phenyl}N—(C=O)—, {$(C_5-C_{25})$aryl}{phenyl}N—(C=O)—, {perhalo$(C_1-C_{20})$alkyl}{phenyl}N—(C=O)—, HO—(C=O)—, $(C_1-C_{20})$alkyl-(C=O)—, $(C_3-C_{25})$heteroaryl-(C=O)—, $(C_3-C_{25})$heterocyclic-(C=O)—, $(C_2-C_{20})$alkenyl-(C=O)—, $(C_3-C_{20})$cycloalkenyl-(C=O)—, $(C_2-C_{20})$alkynyl-(C=O)—, $(C_5-C_{25})$aryl-(C=O)—, perhalo$(C_1-C_{20})$alkyl-(C=O)—, phenyl-(C=O)—, $(C_1-C_{20})$alkyl-O—(C=O)—, $(C_3-C_{25})$heteroaryl-O—(C=O)—, $(C_3-C_{25})$heterocyclic-O—(C=O)—, $(C_2-C_{20})$alkenyl-O—(C=O)—, $(C_3-C_{20})$cycloalkenyl-O—(C=O)—, $(C_2-C_{20})$alkynyl-O—(C=O)—, $(C_5-C_{25})$aryl-O—(C=O), perhalo$(C_1-C_{20})$alkyl-O—(C=O)—, phenyl-O—(C=O)—, $(C_1-C_{20})$alkyl-(C=O)—O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-$ $C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

wherein $R^2$, $R^3$, $R^4$, $R^5$, $R^6$, $R^7$, $R^8$, $R^9$, $R^{10}$, and $R^{11}$ are each independently selected from the group consisting of hydrogen, hydroxy, halo, bromo, chloro, iodo, fluoro, —$N_3$, —CN, —NC, —SH, —$NO_2$, —$NH_2$, ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$)cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, ($C_2$-$C_{20}$)alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2N$—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O){(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkoxy-(C=O){(($C_1$-$C_{20}$)alkyl)N}—, ($C_3$-$C_{25}$)heteroaryl-(C=O){(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$)cycloalkenyl-(C=O){(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O){(($C_1$-$C_{20}$)alkyl)N}—, phenyl-(C=O)NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O){(phenyl)N}—, ($C_3$-$C_{25}$)heteroaryl-(C=O){(phenyl)N}—, ($C_3$-$C_{25}$)heterocyclic-(C=O){(phenyl)N}—, ($C_2$-$C_{20}$)alkenyl-(C=O){(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O){(phenyl)N}—, perhalo($C_1$-$C_{20}$)alkyl-(C=O)-{(phenyl)N}—, $H_2N$(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl)}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{20}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

wherein each of the aforesaid ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_1$-$C_{20}$)cycloalkynyl, and ($C_5$-$C_{25}$)aryl groups (for said $R^2$, $R^3$, $R^4$, $R^5$, $R^6$, $R^7$, $R^8$, $R^9$, $R^{10}$, and $R^{11}$ groups) may be optionally and independently substituted by one to four moieties selected from the group consisting of hydroxy, halo, bromo, chloro, iodo, fluoro, —$N_3$, —CN, —NC, —SH, —$NO_2$, —$NH_2$, ($C_1$-$C_{20}$)alkyl, phenyl, ($C_3$-$C_{20}$)cycloalkyl, ($C_1$-$C_{20}$)alkoxy, ($C_3$-$C_{25}$)heteroaryl, ($C_3$-$C_{25}$)heterocyclic, ($C_2$-$C_{20}$)alkenyl, ($C_3$-$C_{20}$)cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$)cycloalkenyl-O—, ($C_2$-$C_{20}$)alkynyl-O—, ($C_5$-$C_{20}$)cycloalkynyl-O—, ($C_5$-$C_{25}$)aryl-O—, perhalo($C_1$-$C_{20}$)alkyl-O—, ($C_1$-$C_{20}$)alkyl-S—, phenyl-S—, ($C_3$-$C_{20}$)cycloalkyl-S—, ($C_3$-$C_{25}$)heteroaryl-S—, ($C_3$-$C_{25}$)heterocyclic-S—, ($C_2$-$C_{20}$)alkenyl-S—, ($C_3$-$C_{20}$)cycloalkenyl-S—, ($C_2$-$C_{20}$)alkynyl-S—, ($C_5$-$C_{20}$)cycloalkynyl-S—, ($C_5$-$C_{25}$)aryl-S—, perhalo($C_1$-$C_{20}$)alkyl-S—, ($C_1$-$C_{20}$)alkyl-$SO_2$—, phenyl-$SO_2$—, ($C_3$-$C_{20}$)cycloalkyl-$SO_2$—, ($C_1$-$C_{20}$)alkoxy-$SO_2$—, ($C_3$-$C_{25}$)heteroaryl-$SO_2$—, ($C_3$-$C_{25}$)heterocyclic-$SO_2$—, ($C_2$-$C_{20}$)alkenyl-$SO_2$—, ($C_3$-$C_{20}$)cycloalkenyl-$SO_2$—, ($C_2$-$C_{20}$)alkynyl-$SO_2$—, ($C_5$-$C_{20}$)cycloalkynyl-$SO_2$—, ($C_5$-$C_{25}$)aryl-$SO_2$—, perhalo($C_1$-$C_{20}$)alkyl-$SO_2$—, $H_2N$—$SO_2$—, ($C_1$-$C_{20}$)alkyl-NH—$SO_2$—, phenyl-NH—$SO_2$—, ($C_3$-$C_{20}$)cycloalkyl-NH—$SO_2$—, ($C_1$-$C_{20}$)alkoxy-NH—$SO_2$—, ($C_3$-$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$NH—, ($C_2$-$C_{20}$)alkynyl-$SO_2$—NH—, ($C_5$-$C_{20}$)cycloalkynyl-$SO_2$—NH—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)NH—, ($C_3$-$C_{25}$)heterocyclic-(C=O)NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-C=O)—NH—, perhalo($C_1$-$C_{20}$)alkyl-(C=O)NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkyloxy-(C=O)—{(($C_1$-$C_{20}$))alkyl)N}—, ($C_3$-$C_{25}$), heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$)cycloalkenyl-(C=O){(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O){(($C_1$-$C_{20}$)alkyl)N}—, phenyl-(C=O)NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O)-{(phenyl)N}—, perhalo($C_1$-$C_{20}$)alkyl-(C=O)-{(phenyl)N}—, $H_2N$(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O)—, ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}N—(C=O)—, {($C_3$-$C_{20}$)cycloalkyl}{($C_1$-$C_{20}$)alkyl}N—(C=O)—, {($C_1$-$C_{20}$)alkoxy}{($C_1$-$C_{20}$)alkyl}$_2$N—(C=O)—, {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$))alkyl}N—(C=O)—, {($C_3$-$C_{20}$))cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}-(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl)}N—(C=O)—, {($C_2$-$C_{20}$)alkynyl}{phenyl}N—(C=O)—, {($C_5$-$C_{20}$)cycloalkynyl}{phenyl}N<C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_5$-$C_{25}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O), perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

and wherein two independently chosen $R^2$, $R^3$, $R^4$, $R^5$, $R^6$, $R^7$, $R^8$, $R^9$, $R^{10}$, and $R^{11}$ alkyl-containing groups may be taken together with any atom to which they are attached to form a three to forty membered cyclic, heterocyclic or heteroaryl ring;

as a salt of at least one pharmaceutically acceptable acid selected from the group consisting of compounds having the following formulas:

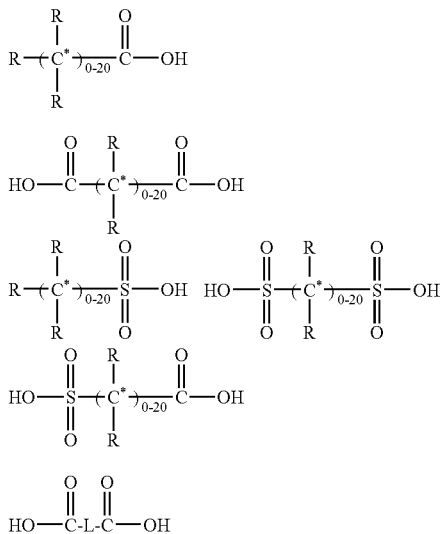

wherein each C* independently represents a potentially chiral carbon that can be in either the D or L enantiomeric configuration;

wherein each R is independently unsubstituted or substituted and selected from the group consisting of Y—, Y—O—, Y—S—, Y—SO$_2$—, (Y)$_2$—N—SO$_2$—, Y—(C=O)—, Y—(C=O)—O—, YO—(C=O)—, (Y)$_2$—N—, Y—(C=O)—(Y—N)—, (Y—(C=O))$_2$—N—, Y—(SO$_2$)—(Y—N)—, or (Y—(SO$_2$))$_2$—N—; each Y being independently selected from the group consisting of hydrogen, carboxyl, halo, hydroxyl, thiol, nitro, amine, NC—, (C$_1$-C$_6$)alkyl, (C$_3$-C$_6$)cycloalkyl, (C$_2$-C$_6$)alkenyl, (C$_3$-C$_6$)cycloalkenyl, (C$_2$-C$_6$)alkynyl, (C$_3$-C$_6$)cycloalkynyl, (C$_1$-C$_6$)alkoxy, (C$_5$-C$_7$)aryl, (C$_3$-C$_5$)heteroaryl, and (C$_3$-C$_5$)heterocyclic; wherein each of the aforesaid (C$_1$-C$_6$)alkyl, (C$_3$-C$_6$)cycloalkyl, (C$_2$-C$_6$)alkenyl, (C$_3$-C$_6$)cycloalkenyl, (C$_2$-C$_6$)alkynyl, (C$_3$-C$_6$)cycloalkynyl, (C$_1$-C$_6$)alkoxy, (C$_5$-C$_7$)aryl, (C$_3$-C$_5$)heteroaryl, and (C$_3$-C$_5$)heterocyclic substituents may be substituted or unsubstituted;

wherein two independently chosen Y alkyl-containing groups may be taken together with any nitrogen atom to which they are attached to form a three to twelve membered cyclic, heterocyclic or heteroaryl ring;

and wherein in the compound having the formula VII, L is a diradical moiety selected from the group consisting of (C$_1$-C$_{20}$)alkyl, (C$_3$-C$_{20}$)cycloalkyl, (C$_2$-C$_{20}$)alkenyl, (C$_3$-C$_{20}$)cycloalkenyl, (C$_2$-C$_{20}$)alkynyl, (C$_3$-C$_{20}$)cycloalkynyl, (C$_1$-C$_{20}$)alkoxy/thiol, (C$_3$-C$_{20}$)aryl, (C$_3$-C$_{15}$)heteroaryl, (C$_3$-C$_{15}$)heterocyclic and (C$_3$-C$_{20}$)cycloalkyl; wherein each of the aforesaid (C$_1$-C$_{20}$)alkyl, (C$_3$-C$_{20}$)cycloalkyl, (C$_2$-C$_{20}$)alkenyl, (C$_3$-C$_{20}$)cycloalkenyl, (C$_2$-C$_{20}$)alkynyl, (C$_3$-C$_{20}$)cycloalkynyl, (C$_1$-C$_{20}$)alkoxy/thiol, (C$_3$-C$_{20}$)aryl, (C$_3$-C$_{15}$)heteroaryl, (C$_3$-C$_{15}$)heterocyclic and (C$_3$-C$_{20}$)cycloalkyl diradical moieties may be substituted or unsubstituted.

Another embodiment of the invention provides a pharmaceutically acceptable composition, comprising the salt described above in contact with at least one pharmaceutically acceptable carrier.

Another embodiment of the invention provides a method, comprising administering the salt or the pharmaceutically acceptable composition described above to a human.

DETAILED DESCRIPTION OF THE INVENTION

It has been found that certain select acids form salts with guanylhydrazone compounds producing guanylhydrazone salts having a number of advantages over known salts of guanylhydrazone compounds. These guanylhydrazone salts have been found to have an unexpectedly superior combination of formulation and solubility advantages which make them particularly suitable for the preparation of pharmaceutical formulations containing guanylhydrazone-containing drugs.

Thus, according to the present invention, there are provided improved salts of guanylhydrazone containing compounds. In a preferred embodiment, the inventive salts relate to salts of complex guanylhydrazone compounds (i.e., compounds that contain multiple guanylhydrazone moieties). In a most preferred embodiment, the complex guanylhydrazone compound is Semapimod:

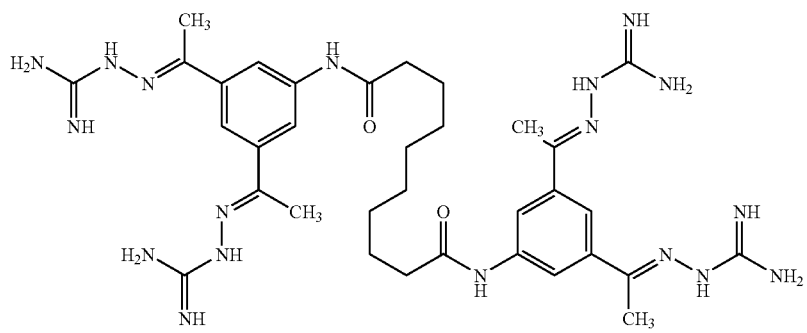

CNI-1493

The Semapimod compound (sometimes referred to herein as CNI-1493 is identified as Compound No. 14 in U.S. Pat. No. 5,599,984 to Bianchi et al., the entire contents of which are hereby incorporated by reference.

The invention also relates to alternative pharmaceutical dosage formats involving the guanylhydrazone salts of the invention. The alternative formats include, for example, hard gelatin capsules or quick release tablets for oral consumption, compositions for topical application, or various solutions for parenteral injection (including, but not limited to subcutaneous and intramuscular) or infusion. In addition, the guanylhydrazone salts of the invention provide improved storage capabilities for the active agent compound in an improved stable format.

Other aspects of the invention relate to methods of making the guanylhydrazone salts according to the invention.

Other aspects of the invention relate to methods of using the inventive guanylhydrazone salts in various applications such as screening assays, efficacy and safety tests, and in therapies or treatments. These methods of use involve, among other things, in vitro testing and in vivo testing. The inventive guanylhydrazone salts can also be used in therapeutic methods for which a guanylhydrazone compound has previously been identified as effective as the active agent, but which heretofore have not been identified in an improved salt form for enhanced delivery and bioavailability.

According to one embodiment, a guanylhydrazone salt according to the invention includes one or more guanylhydrazone compounds combined with a carboxylic acid. One suitable carboxylic acid for the salt combination includes a chemical structure having one of the following formulas (I and II):

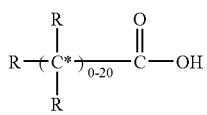

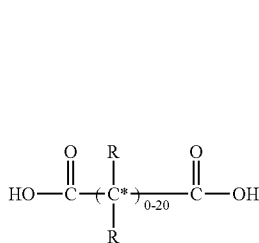

In the carboxylic acid formulas I and II above, C* represents a potentially chiral carbon that can be in either the D or L enantiomeric configuration, and R represents a suitable substituent such as, but not limited to, hydrogen (H), or methyl ($CH_3$) or other alkyl. The "0-20" range includes all values and subranges therebetween, including 0, 1, 2, 3, 4, 5, 6, 7, 8, 9, 10, 11, 12, 13, 14, 15, 16, 17, 18, 19 and 20.

More particularly, in the carboxylic acid formulas I and II above, each R may be independently selected from Y—, Y—O—, Y—S—, Y—$SO_2$—, $(Y)_2$—N—$SO_2$—, Y—(C═O), Y—(C═O)—O—, YO—(C═O)—, $(Y)_2$—N—, Y—(C═O)—(Y—N)—, (Y—(C═O))$_2$—N—, Y—($SO_2$)—(Y—N)—, or (Y—($SO_2$))$_2$—N—; wherein two independently chosen Y alkyl-containing groups may be taken together with any nitrogen atom to which they are attached to form a three to twelve membered cyclic, heterocyclic or heteroaryl ring, and each Y is independently selected from hydrogen, carboxyl, halo, hydroxyl, thiol, nitro, amine, NC—, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_3$-$C_6$)cycloalkynyl, ($C_1$-$C_6$)alkoxy, ($C_5$-$C_7$)aryl, ($C_3$-$C_5$)heteroaryl, and ($C_3$-$C_5$) heterocyclic; wherein each of the aforesaid ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_3$-$C_6$)cycloalkynyl, ($C_1$-$C_6$)alkoxy, ($C_5$-$C_7$)aryl, ($C_3$-$C_5$)heteroaryl, and ($C_3$-$C_5$)heterocyclic substituents may optionally be substituted with one or more suitable substituents described herein, as in for instance a halo-substituted alkyl, by one to ten moieties independently selected from the group consisting of carboxyl, halo, hydroxyl, thiol, nitro, amine, NC—, ($C_1$-$C_4$)alkyl, ($C_1$-$C_4$) alkoxy, ($C_2$-$C_4$)alkenyl, and ($C_2$-$C_4$)alkynyl.

According to another embodiment, the carboxylic acid in the guanylhydrazone salt is described by the following general formula (III):

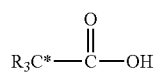

wherein C* and each R, independently, are defined as described for the carboxylic acid formulas I and II above. In one aspect of this embodiment the carboxylic acid is acetic acid:

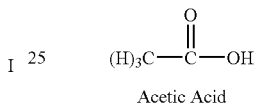

Acetic Acid

According to another embodiment, the carboxylic acid in the guanylhydrazone salt according to the invention is described by the following general formula (IV):

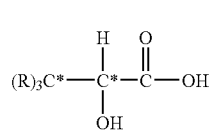

wherein C* and R are defined as described for the carboxylic acid formulas I and II above. In one aspect of this embodiment the carboxylic acid is L-lactic acid:

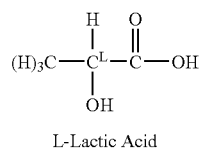

L-Lactic Acid

According to another embodiment, the carboxylic acid in the guanylhydrazone salt according to the invention is described by the following general formula (V):

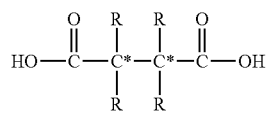

wherein C* and R are defined as described for the carboxylic acid formulas I and II above. In one aspect of this embodiment the carboxylic acid is L-Aspartic Acid:

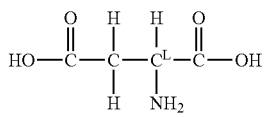

L-Aspartic Acid

According to another embodiment, the carboxylic acid in the guanylhydrazone salt according to the invention is described by the following general formula (VI):

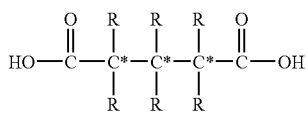

VI wherein C* and R are defined as described for the carboxylic acid formulas I and II above. In one aspect of this embodiment the carboxylic acid is L-glutamic acid:

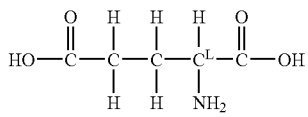

L-Glutamic Acid

According to another embodiment, the guanylhydrazone-carboxylic acid salts according to the invention include a guanylhydrazone compound combined with a carboxylic acid wherein a suitable carboxylic acid for the salt combination, according to this embodiment, is a chemical structure described by the following general formula (VII):

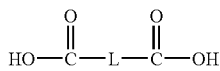

VII wherein L is a diradical moiety selected from a $(C_1-C_{20})$ alkyl, $(C_3-C_{20})$cycloalkyl, $(C_2-C_{20})$alkenyl, $(C_3-C_{20})$cycloalkenyl, $(C_2-C_{20})$alkynyl, $(C_3-C_{20})$cycloalkynyl, $(C_1-C_{20})$ alkoxy/thiol, $(C_3-C_{20})$aryl, $(C_3-C_{15})$heteroaryl, $(C_3-C_{15})$ heterocyclic and $(C_3-C_{20})$cycloalkyl; wherein each of the aforesaid $(C_1-C_{20})$alkyl, $(C_3-C_{20})$cycloalkyl, $(C_2-C_{20})$alkenyl, $(C_3-C_{20})$cycloalkenyl, $(C_2-C_{20})$alkynyl, $(C_3-C_{20})$cycloalkynyl, $(C_1-C_{20})$alkoxy/thiol, $(C_3-C_{20})$aryl, $(C_3-C_{15})$heteroaryl, $(C_3-C_{15})$heterocyclic and $(C_3-C_{20})$cycloalkyl diradical moieties may optionally be substituted, for example, with one or more suitable substituents defined herein, for example a halo-substituted alkyl, by one to twenty moieties independently selected from the group including carboxyl, halo, hydroxyl, thiol, nitro, amine, Y or R wherein these terms are defined herein.

According to another embodiment, the anion for the guanylhydrazone salt may be described by one of the following general formulas:

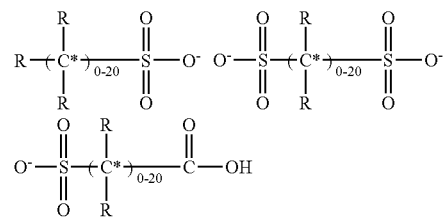

wherein C* and R represent suitable substituents as defined herein. The monovalent form of the above divalent anion is also suitable.

In another embodiment, the acid form of the guanylhydrazone salt may have one of the following formulas:

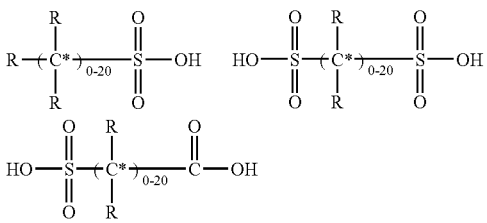

Either the monovalent or divalent anion forms of the acids are suitable.

According to another embodiment, the anion in the guanylhydrazone salt according to the invention is described by the following general formula:

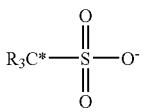

In one aspect of this embodiment, the anion is mesylate.
Of course, the acid form of the above anion may be described as follows:

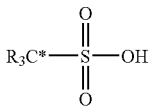

In the compounds herein, a "suitable substituent" is intended to mean a functional group that does not negate the intended activity of the active guanylhydrazone compound in the salt. For example, the suitable substituent would not negate the activity of the guanylhydrazone compound. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. Combinations of substituents are possible.

As used herein, the term, "alkylene" refers to a diradical alkane species that contains 1, 2, 3, 4, 5, 6, 7, 8, 9, 10, 11, 12, 13, 14, 15, 16, 17, 18, 19 and 20 carbons or any subrange of carbons therebetween. The alkylene may be branched or unbranched, saturated or unsaturated, and substituted or unsubstituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl. In addition, any carbon atom therein may be optionally replaced with one or more heteroatoms such as nitrogen, oxygen or sulfur or any combination thereof.

As used herein, the term, "cycloalkylene" refers to a diradical cycloalkane species that contains 3, 4, 5, 6, 7, 8, 9, 10, 11, 12, 13, 14, 15, 16, 17, 18, 19 and 20 ring carbons or any subrange of carbons therebetween. The cycloalkylene may be branched or unbranched, saturated or unsaturated, and substituted or unsubstituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl. In addition, any carbon atom therein may be optionally replaced with one or more heteroatom such as nitrogen, oxygen or sulfur or any combination thereof.

As used herein, the term "arylene" means an aromatic diradical species having 5, 6, 7, 8, 9, 10, 11, 12, 13, 14, 15, 16, 17, 18, 19, 20, 21, 22, 23, 24 and 25 carbons and any subrange of carbons thereof. These may be unsubstituted or substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl. In addition, any carbon atom therein may be optionally replaced with one or more heteroatom such as nitrogen, oxygen or sulfur or any combination thereof to form a heteroarylene.

As used herein, the term "alkyl" as well as the alkyl moieties of or within other groups referred to herein (e.g., ($C_1$-$C_{20}$)alkyl, ($C_1$-$C_{20}$)alkoxy, ($C_2$-$C_{20}$)alkenyl, ($C_2$-$C_{20}$)alkynyl, and perhalo($C_1$-$C_{20}$)alkyl) include alkyl moieties having 1, 2, 3, 4, 5, 6, 7, 8, 9, 10, 11, 12, 13, 14, 15, 16, 17, 18, 19 and 20 carbons or any subrange of carbons therebetween. They may be linear or branched (such as methyl, ethyl, n-propyl, isopropyl, n-butyl, iso-butyl, secondary-butyl, tertiary-butyl, etc.). They may be saturated or unsaturated as indicated by the "alkenyl" or "alkynyl" terminology. Other than the perhaloalkyl, which are completely substituted by one or more of the same or different halogens, the alkyl groups may be unsubstituted or substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl.

As used herein, the term "cycloalkyl" as well as the other moieties having cyclic groups referred to herein (for example ($C_3$-$C_{20}$)cycloalkyl, ($C_3$-$C_{20}$)cycloalkenyl and ($C_5$-$C_{20}$)cycloalkynyl) refers to mono carbocyclic moieties having 3, 4, 5, 6, 7, 8, 9, 10, 11, 12, 13, 14, 15, 16, 17, 18, 19 and 20 ring carbons or any subrange of carbons therebetween. They may be unsubstituted or substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl.

As used herein, the terms, "alkenyl," "alkynyl," "cycloalkynyl," and "cycloalkenyl" refer to unsaturated radical species having 1, 2, 3, 4, 5, 6, 7, 8, 9, 10, 11, 12, 13, 14, 15, 16, 17, 18, 19 and 20 carbons (or, for the cyclic species 3, 4, 5, 6, 7, 8, 9, 10, 11, 12, 13, 14, 15, 16, 17, 18, 19 and 20 ring carbons) or any subrange of carbons or ring carbons therebetween. They may be branched or unbranched, and they may be unsubstituted or substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl. These groups have one or more than one site of unsaturation, i.e., one or more double or triple bonds. For example, these moieties may have one, two, three, four or more sites of unsaturation. Some nonlimiting examples of these include ethenyl, 1-propenyl, 2-propenyl (allyl), iso-propenyl, 2-methyl-1-propenyl, 1-butenyl, 2-butenyl, ethynyl, 1-propynyl, 2-propynyl, 1-butynyl, and 2-butynyl.

As used herein, the term, "alkoxy" refers to alkyl-O— radical species having 1, 2, 3, 4, 5, 6, 7, 8, 9, 10, 11, 12, 13, 14, 15, 16, 17, 18, 19 and 20 carbons or any subrange of carbons therebetween. They may be unsubstituted or substituted with one or more suitable substituents defined herein, for example with one or more fluoro, chloro, trifluoromethyl, ($C_1$-$C_3$) alkoxy, trifluoromethoxy, difluoromethoxy or ($C_1$-$C_3$)alkyl.

As used herein, the term "halogen" or "halo" includes fluoro, chloro, bromo or iodo, and any combination thereof.

As used herein, the term "aryl" means aromatic radicals having 5, 6, 7, 8, 9, 10, 11, 12, 13, 14, 15, 16, 17, 18, 19, 20, 21, 22, 23, 24 and 25-carbons and any subrange of carbons thereof. These may be unsubstituted or substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl. Nonlimiting examples include phenyl, naphthyl, tetrahydronaphthyl, indanyl and the like.

As used herein, the term "heteroaryl" refers to an aromatic heterocyclic group with at least one heteroatom selected from O, S and N in the ring and having 3, 4, 5, 6, 7, 8, 9, 10, 11, 12, 13, 14, 15, 16, 17, 18, 19, 20, 21, 22, 23, 24 and 25 ring carbons and any subrange of carbons thereof. The heteroatoms may be present either alone or in any combination. The heteroaryl groups may be unsubstituted or substituted with one or more suitable substituents defined herein, for example with one or more fluoro, chloro, trifluoromethyl, ($C_1$-$C_3$) alkoxy, trifluoromethoxy, difluoromethoxy or ($C_1$-$C_3$)alkyl. One, two, three, four or more heteroatoms may be present. In addition to the heteroatom, the aromatic group may optionally have up to four N atoms in the ring. Nonlimiting examples of heteroaryl groups include pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; which are optionally unsubstituted or substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl.

The term "heterocyclic" as used herein refers to a cyclic group containing 3, 4, 5, 6, 7, 8, 9, 10, 11, 12, 13, 14, 15, 16, 17, 18, 19, 20, 21, 22, 23, 24 and 25 ring carbons and any subrange of carbons thereof carbon atoms and hetero atoms selected from N, O, S or NR'. Nonlimiting examples include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl and the like. Examples of such monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl and the like; which may be unsubstituted or optionally substituted with one or more suitable substituents defined herein, for example with one or more fluoro, chloro, trifluoromethyl, ($C_1$-$C_3$)alkoxy, trifluoromethoxy, difluoromethoxy or ($C_1$-$C_3$)alkyl. R' can be any suitable substituent, for example Y as defined herein, or more preferably methyl.

As used herein, the term "halo-substituted alkyl" refers to an alkyl radical as described above substituted with one or more halogens including, but not limited to, chloromethyl, dichloromethyl, fluoromethyl, difluoromethyl, trifluoromethyl, 2,2,2-trichloroethyl, and the like; optionally further substituted with one or more suitable substituents defined herein, for example fluoro, chloro, trifluoromethyl, ($C_1$-$C_3$) alkoxy, trifluoromethoxy, difluoromethoxy or ($C_1$-$C_3$)alkyl.

As used herein, the term "carbonyl" or "(C=O)" (as used in phrases such as alkylcarbonyl, alkyl-(C=O)— or alkoxycarbonyl) refers to the joinder of the C=O moiety to a second moiety such as an alkyl or amino group (i.e., an amido group). Alkoxycarbonylamino (i.e., alkoxy(C=O)—NH—) refers to an alkyl carbamate group. The carbonyl group is also equivalently defined herein as (C=O). Alkylcarbonylamino refers to groups such as acetamide.

One preferred embodiment of this invention is a salt wherein a guanylhydrazone compound is combined with L-Lactic Acid. In a more preferred embodiment, the salt is guanylhydrazone compound containing multiple guanylhydrazone moieties and combined with L-Lactic Acid. In a most preferred embodiment, the invention relates to a salt combining the guanylhydrazone-containing compound with L-Lactic Acid.

In another embodiment, the invention relates to a guanylhydrazone compound, for example Semapimod, combined with other acids to form a pharmaceutically acceptable salt. The acids which are used to prepare the pharmaceutically acceptable acid addition salts of the guanylhydrazone compounds invention include those which form non-toxic acid addition salts, i.e., salts containing pharmacologically acceptable anions, such as the chloride, bromide, iodide, nitrate, sulfate, bisulfate, phosphate, acid phosphate, diphosphate, citrate, acid citrate, tartrate, bitartrate, succinate, fumarate, tosylate, mesylate, gluconate, saccharate, benzoate, methanesulfonate, ethanesulfonate, benzenesulfonate, p-toluenesulfonate, pamoate (i.e., 1,1'-methylene-bis-(2-hydroxy-3-naphthoate)), bicarbonate, edetate, camsylate, carbonate, dihydrochloride, edentate, edisylate, estolate, esylate, fumarate, gluceptate, glucoheptonate, gluconate, glutamate, glycollylarsanilate, hexylresorcinate, hydrabamine, hydrobromide, hydrochloride, hydroxynaphthoate, isethionate, lactate, lactobionate, malate, mandelate, methylbromide, methylnitrate, methylsulfate, mucate, napsylate, pantothenate, polygalacturonate, salicylate, stearate, subacetate, succinate, tannate, teoclate, and triethiodide salts. Mixtures of salts are possible.

Any ratio of guanylhydrazone:counterion in the salt form, for example, guanylhydrazone:counterion ratios of 10, 9, 8, 7, 6, 5, 4, 3, 2, 1:1, 2, 3, 4, 5, 6, 7, 8, 9, 10 is suitable. The ratio can be expressed as the number of "Ghy" groups counterions or as the number of ionic guanylhydrazone molecules:counterions as appropriate. In one embodiment, either the guanylhydrazone or the counterion or both may be multivalent, and the ratio is adjusted accordingly such that the salt may adopt a zero or non-zero charge. Mixed salts are possible.

Other suitable salts include those of the guanylhydrazone compounds having the formula:

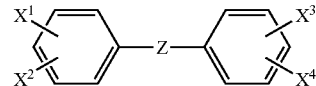

wherein $X^1$, $X^2$, $X^3$, and $X^4$ each independently represent H, GhyCH—, GhyCCH$_3$—, or CH$_3$CO—, with the provisos that $X^1$, $X^2$, $X^3$ and $X^4$ are not simultaneously H;

wherein Z is one or more selected from the group consisting of:

-($A^1$)$_a$-(CR$^2$R$^3$)$_x$-($A^2$)$_b$-;
-($A^1$)$_a$-(CR$^2$R$^3$)$_x$-Q$_m$-(CR$^4$R$^5$)$_y$-($A^2$)$_b$-; and
-($A^1$)$_a$-(CR$^2$R$^3$)$_x$-Q$_m$-(CR$^4$R$^5$)$_y$-T$_n$-(CR$^6$R$^7$)$_z$-($A^2$)$_b$;

and combinations thereof;

wherein a is selected from the group consisting of 0, 1, 2, 3, 4, 5, 6, 7, 8, and 9;

wherein b is selected from the group consisting of 0, 1, 2, 3, 4, 5, 6, 7, 8, and 9;

wherein x is selected from the group consisting of 0, 1, 2, 3, 4, 5, 6, 7, 8, and 9;

wherein y is selected from the group consisting of 0, 1, 2, 3, 4, 5, 6, 7, 8, and 9;

wherein z is selected from the group consisting of 0, 1, 2, 3, 4, 5, 6, 7, 8, and 9;

wherein m is selected from the group consisting of 0, 2, 3, 4, 5, 6, 7, 8, and 9;

wherein n is selected from the group consisting of 0, 1, 2, 3, 4, 5, 6, 7, 8, and 9;

wherein $A^1$ and $A^2$ are each independently selected from the group consisting of —NR$^8$(CO)NR$^9$—, —(CO)NR$^8$—, —NR$^8$(CO)—, —NR$^8$—, —O—, —S—, —S(=O)—, —SO$_2$—, —SO$_2$NR$^8$—, —NR$^8$SO$_2$—, and salts thereof;

wherein Q and T are each independently selected from the group consisting of —NR$^{10}$(CO)NR$^{11}$—, —(CO)NR$^{10}$—, —NR$^{10}$(CO)—, NR$^{10}$—, —O—, —S—, —S(=O)—, —SO$_2$—, —SO$_2$NR$^{10}$—, —NR$^{10}$SO$_2$—, salts thereof, branched or unbranched, saturated or unsaturated, substituted or unsubstituted $C_1$-$C_{20}$ alkylene, saturated or unsaturated, substituted or unsubstituted $C_3$-$C_{20}$ cycloalkylene, substituted or unsubstituted $C_5$-$C_{25}$ arylene, and combinations thereof;

wherein one or more carbon atoms in any of said alkylene, cycloalkylene or arylene in said Q and/or T may each be independently replaced with one or more heteroatoms selected from the group consisting of nitrogen, oxygen, sulfur, and a combination thereof;

and wherein when substituted, said alkylene, cycloalkylene or arylene in said Q and/or T are each independently substituted with one or more substituent groups selected from the group consisting of hydroxy, halo, bromo, chloro, iodo, fluoro, —N$_3$, —CN, —NC, —SH, —NO$_2$, —NH$_2$, ($C_1$-$C_{20}$) alkyl, phenyl, ($C_3$-$C_{20}$)cycloalkyl, ($C_1$-$C_{20}$)alkoxy, ($C_3$-$C_{25}$) heteroaryl, ($C_3$-$C_{25}$)heterocyclic, ($C_2$-$C_{20}$)alkenyl, ($C_3$-$C_{20}$) cycloalkenyl, ($C_2$-$C_{20}$)alkynyl, ($C_5$-$C_{20}$)cycloalkynyl, ($C_5$-$C_{25}$)aryl, perhalo($C_1$-$C_{20}$)alkyl, ($C_1$-$C_{20}$)alkyl-O—, phenyl-O—, ($C_3$-$C_{20}$)cycloalkyl-O—, ($C_3$-$C_{25}$)heteroaryl-O—, ($C_3$-$C_{25}$)heterocyclic-O—, ($C_2$-$C_{20}$)alkenyl-O—, ($C_3$-$C_{20}$) cycloalkenyl-O—, ($C_2$-$C_{20}$)alkynyl-O—, ($C_5$-$C_{20}$) cycloalkynyl-O—, ($C_5$-$C_{25}$)aryl-O—, perhalo($C_1$-$C_{20}$)alkyl- O—, $(C_1-C_{20})$alkyl-S—, phenyl-S—, $(C_3-C_{20})$cycloalkyl-S—, $(C_3-C_{25})$heteroaryl-S—, $(C_3-C_{25})$heterocyclic-S—, $(C_2-C_{20})$alkenyl-S—, $(C_3-C_{20})$cycloalkenyl-S—, $(C_2-C_{20})$alkynyl-S—, $(C_5-C_{20})$cycloalkynyl-S—, $(C_5-C_{25})$aryl-S—, perhalo$(C_1-C_{20})$alkyl-S—, $(C_1-C_{20})$alkyl-SO$_2$—, phenyl-SO$_2$—, $(C_3-C_{20})$cycloalkyl-SO$_2$—, $(C_1-C_{20})$alkoxy-SO$_2$—, $(C_3-C_{25})$heteroaryl-SO$_2$—, $(C_3-C_{25})$heterocyclic-SO$_2$—, $(C_2-C_{20})$alkenyl-SO$_2$—, $(C_3-C_{20})$cycloalkenyl-SO$_2$—, $(C_2-C_{20})$alkynyl-SO$_2$—, $(C_5-C_{20})$cycloalkynyl-SO$_2$—, $(C_5-C_{25})$aryl-SO$_2$—, perhalo$(C_1-C_{20})$alkyl-SO$_2$—, H$_2$N—SO$_2$—, $(C_1-C_{20})$alkyl-NH—SO$_2$—, phenyl-NH—SO$_2$—, $(C_3-C_{20})$cycloalkyl-NH—SO$_2$—, $(C_1-C_{20})$alkoxy-NH—SO$_2$—, $(C_3-C_{25})$heteroaryl-NH—SO$_2$—, $(C_3-C_{25})$heterocyclic-NH—SO$_2$—, $(C_2-C_{20})$alkenyl-NH—SO$_2$—, $(C_3-C_{20})$cycloalkenyl-NH—SO$_2$—, $(C_2-C_{20})$alkynyl-NH—SO$_2$—, $(C_5-C_{20})$cycloalkynyl-NH—SO$_2$—, $(C_5-C_{25})$aryl-NH—SO$_2$—, perhalo$(C_1-C_{20})$alkyl-NH—SO$_2$—, {$(C_1-C_{20})$alkyl}$_2$N—SO$_2$—, {phenyl}$_2$N—SO$_2$—, {$(C_3-C_{20})$cycloalkyl}$_2$N—SO$_2$—, {$(C_1-C_{20})$alkoxy}$_2$N—SO$_2$—, {$(C_3-C_{25})$heteroaryl}$_2$N—SO$_2$—, {$(C_3-C_{25})$heterocyclic}$_2$N—SO$_2$—, {$(C_2-C_{20})$alkenyl}$_2$N—SO$_2$—, {$(C_2-C_{20})$alkynyl}$_2$N—SO$_2$—, {$(C_5-C_{20})$cycloalkynyl}$_2$N—SO$_2$—, {$(C_5-C_{25})$aryl}$_2$N—SO$_2$—, {perhalo$(C_1-C_{20})$alkyl}$_2$N—SO$_2$—, $(C_1-C_{20})$alkyl-SO$_2$—NH—, phenyl-SO$_2$—NH—, $(C_3-C_{20})$cycloalkyl-SO$_2$—NH—, $(C_1-C_{20})$alkoxy-SO$_2$—NH—, $(C_3-C_{25})$heteroaryl-SO$_2$—NH—, $(C_3-C_{25})$heterocyclic-SO$_2$—NH—, $(C_2-C_{20})$alkenyl-SO$_2$—NH—, $(C_3-C_{20})$cycloalkenyl-SO$_2$—NH—, $(C_2-C_{20})$alkynyl-SO$_2$—NH—, $(C_5-C_{20})$cycloalkynyl-SO$_2$—NH—, $(C_5-C_{25})$aryl-SO$_2$—NH—, perhalo$(C_1-C_{20})$alkyl-SO$_2$—NH—, $(C_1-C_{20})$alkyl-NH—, phenyl-NH—, $(C_3-C_{20})$cycloalkyl-NH—, $(C_1-C_{20})$alkoxy-NH—, $(C_3-C_{25})$heteroaryl-NH—, $(C_3-C_{25})$heterocyclic-NH—, $(C_2-C_{20})$alkenyl-NH—, $(C_3-C_{20})$cycloalkenyl-NH—, $(C_2-C_{20})$alkynyl-NH—, $(C_5-C_{20})$cycloalkynyl-NH—, $(C_5-C_{25})$aryl-NH—, perhalo$(C_1-C_{20})$alkyl-NH—, {$(C_1-C_{20})$alkyl}$_2$N—, {phenyl}$_2$N—, {$(C_3-C_{20})$cycloalkyl}$_2$N—, {$(C_1-C_{20})$alkoxy}$_2$N—, {$(C_3-C_{25})$heteroaryl}$_2$N—, {$(C_3-C_{25})$heterocyclic}$_2$N—, {$(C_2-C_{20})$alkenyl}$_2$N—, {$(C_3-C_{20})$cycloalkenyl}$_2$N—, {$(C_2-C_{20})$alkynyl}$_2$N—, {$(C_5-C_{20})$cycloalkynyl}$_2$N—, {$(C_5-C_{25})$aryl}$_2$N—, {perhalo$(C_1-C_{20})$alkyl}$_2$N—, $(C_1-C_{20})$alkyl-(C=O)—NH—, phenyl-(C=O)—NH—, $(C_3-C_{20})$cycloalkyl-(C=O)—NH—, $(C_1-C_{20})$alkoxy-(C=O)—NH—, $(C_3-C_{25})$heteroaryl-(C=O)—NH—, $(C_3-C_{25})$heterocyclic-(C=O)—NH—, $(C_2-C_{20})$alkenyl-(C=O)NH—, $(C_3-C_{20})$cycloalkenyl-(C=O)—NH—, $(C_2-C_{20})$alkynyl-(C=O)NH—, $(C_5-C_{20})$cycloalkynyl-(C=O)—NH—, $(C_5-C_{25})$aryl-(C=O)—NH—, perhalo$(C_1-C_{20})$alkyl-(C=O—NH—, $(C_1-C_{20})$alkyl-(C=O)—{$((C_1-C_{20})$alkyl)N}—, phenyl-(C=O){$((C_1-C_{20})$alkyl)N}—, $(C_3-C_{20})$cycloalkyl-(C=O)—{$((C_1-C_{20})$alkyl)N}—, $(C_1-C_{20})$alkoxy-(C=O){$((C_1-C_{20})$alkyl)N}—, $(C_3-C_{25})$heteroaryl-(C=O)—{$((C_1-C_{20})$alkyl)N}—, $(C_3-C_{25})$heterocyclic-(C=O)—{$((C_1-C_{20})$alkyl)N}—, $(C_2-C_{20})$alkenyl-(C=O)—{$((C_1-C_{20})$alkyl)N}—, $(C_3-C_{20})$cycloalkenyl-(C=O)—{$((C_1-C_{20})$alkyl)N}—, $(C_2-C_{20})$alkynyl-(C=O){$((C_1-C_{20})$alkyl)N}—, $(C_5-C_{20})$cycloalkynyl-(C=O){$((C_1-C_{20})$alkyl)N}—, $(C_5-C_{25})$aryl-(C=O)—{$((C_1-C_{20})$alkyl)N}—, perhalo$(C_1-C_{20})$alkyl-(C=O)—{$((C_1-C_{20})$alkyl)N}—, phenyl-(C=O)—NH—, phenyl-(C=O)-{(phenyl)N}—, $(C_1-C_{20})$alkyl-(C=O)-{(phenyl)N}—, $(C_3-C_{20})$cycloalkyl-(C=O)-{(phenyl)N}—, $(C_1-C_{20})$alkoxy-(C=O)-{(phenyl)N}—, $(C_3-C_{25})$heteroaryl-(C=O)-{(phenyl)N}—, $(C_3-C_{25})$heterocyclic-(C=O)-{(phenyl)N}—, $(C_2-C_{20})$alkenyl-(C=O)-{(phenyl)N}—, $(C_3-C_{20})$cycloalkenyl-(C=O)-{(phenyl)N}—, $(C_2-C_{20})$alkynyl-(C=O)-{(phenyl)N}—, $(C_5-C_{20})$cycloalkynyl-(C=O)-{(phenyl)N}—, $(C_5-C_{25})$aryl-(C=O)-{(phenyl)N}—, perhalo$(C_1-C_{20})$alkyl-(C=O)-{(phenyl)N}—, H$_2$N(C=O)—, $(C_1-C_{20})$alkyl-NH—(C=O)—, phenyl-NH—(C=O)—, $(C_3-C_{20})$cycloalkyl-NH—(C=O)—, $(C_1-C_{20})$alkoxy-NH—(C=O)—, $(C_3-C_{25})$heteroaryl-NH—(C=O)—, $(C_3-C_{25})$heterocyclic-NH—(C=O)—, $(C_2-C_{20})$alkenyl-NH—(C=O)—, $(C_3-C_{20})$cycloalkenyl-NH—(C=O)—, $(C_2-C_{20})$alkynyl-NH—(C=O)—, $(C_5-C_{20})$cycloalkynyl-NH—(C=O)—, $(C_5-C_{25})$aryl-NH—(C=O)—, perhalo$(C_1-C_{20})$alkyl-NH—(C=O)—, {$(C_1-C_{20})$alkyl}$_2$N—(C=O)—, {phenyl}{$(C_1-C_{20})$alkyl}N—(C=O)—, {$(C_3-C_{20})$cycloalkyl}{$(C_1-C_{20})$alkyl}N—(C=O)—, {$(C_1-C_{20})$alkoxy}{$(C_1-C_{20})$alkyl}N—(C=O)—, {$(C_3-C_{25})$heteroaryl}{$(C_1-C_{20})$alkyl}N—(C=O)—, {$(C_3-C_{25})$heterocyclic}{$(C_1-C_{20})$alkyl}N—(C=O)—, {$(C_2-C_{20})$alkenyl}{$(C_1-C_{20})$alkyl}N—(C=O)—, {$(C_3-C_{20})$cycloalkenyl}{$(C_1-C_{20})$alkyl}N—(C=O)—, {$(C_2-C_{20})$alkynyl}{$(C_1-C_{20})$alkyl}N—(C=O)—, {$(C_5-C_{20})$cycloalkynyl}{$(C_1-C_{20})$alkyl}N—(C=O)—, {$(C_5-C_{25})$aryl}{$(C_1-C_{20})$alkyl}N—(C=O)—, {perhalo$(C_1-C_{20})$alkyl}{$(C_1-C_{20})$alkyl}N—(C=O)—, {phenyl}$_2$N—(C=O)—, {$(C_3-C_{20})$cycloalkyl}{phenyl}N—(C=O)—, {$(C_1-C_{20})$alkoxy}{phenyl}N—(C=O)—, {$(C_3-C_{25})$heteroaryl}{phenyl}N—(C=O)—, {$(C_3-C_{25})$heterocyclic}{phenyl}N—(C=O), {$(C_3-C_{20})$alkenyl}{phenyl}N—(C=O)—, {$(C_3-C_{20})$cycloalkenyl}{phenyl}N—(C=O)—, {$(C_2-C_{20})$alkynyl}{phenyl}N—(C=O)—, {$(C_5-C_{20})$cycloalkynyl}{phenyl}N—(C=O)—, {$(C_5-C_{25})$aryl}{phenyl}N—(C=O)—, {perhalo$(C_1-C_{20})$alkyl}{phenyl}N—(C=O)—, HO—(C=O)—, $(C_1-C_{20})$alkyl-(C=O)—, $(C_3-C_{25})$heteroaryl-(C=O)—, $(C_3-C_{25})$heterocyclic-(C=O)—, $(C_2-C_{20})$alkenyl-(C=O)—, $(C_3-C_{20})$cycloalkenyl-(C=O)—, $(C_2-C_{20})$alkynyl-(C=O)—, $(C_5-C_{25})$aryl-(C=O)—, perhalo$(C_1-C_{20})$alkyl-(C=O)—, phenyl-(C=O)—, $(C_1-C_{20})$alkyl-O—(C=O)—, $(C_3-C_{25})$heteroaryl-O—(C=O)—, $(C_3-C_{25})$heterocyclic-O—(C=O)—, $(C_2-C_{20})$alkenyl-O—(C=O)—, $(C_3-C_{20})$cycloalkenyl-O—(C=O)—, $(C_2-C_{20})$alkynyl-O—(C=O)—, $(C_5-C_{25})$aryl-O—(C=O)—, perhalo$(C_1-C_{20})$alkyl-O—(C=O)—, phenyl-O—(C=O)—, $(C_1-C_{20})$alkyl-(C=O)—O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-C_{20})$cycloalkenyl-(C=O)—O—, $(C_2-C_{20})$alkynyl-(C=O)—O—, $(C_5-C_{25})$aryl-(C=O)—O—, phenyl-(C=O)—O—, perhalo$(C_1-C_{20})$alkyl-(C=O)—O—, and salts thereof;

wherein each of the aforesaid $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, and $(C_5-C_{25})$aryl groups (as substituents on said alkylene, cycloalkylene or arylene of said Q and T) may be optionally and independently substituted by one to four moieties selected from the group consisting of hydroxy, halo, bromo, chloro, iodo, fluoro, —N$_3$, —CN, —NC, —SH, —NO$_2$, —NH$_2$, $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, $(C_5-C_{25})$aryl, perhalo$(C_1-C_{20})$alkyl, $(C_1-C_{20})$alkyl-O—, phenyl-O—, $(C_3-C_{20})$cycloalkyl-O—, $(C_3-C_{25})$heteroaryl-O—, $(C_3-C_{25})$heterocyclic-O—, $(C_2-C_{20})$alkenyl-O—, $(C_3-C_{20})$cycloalkenyl-O—, $(C_2-C_{20})$alkynyl-O—, $(C_5-C_{20})$cycloalkynyl-O—, $(C_5-C_{25})$aryl-O—, perhalo$(C_1-C_{20})$alkyl-O—, $(C_1-C_{20})$alkyl-S—, phenyl-S—, $(C_3-C_{20})$cycloalkyl-S—, $(C_3-C_{25})$heteroaryl-S—, $(C_3-C_{25})$heterocyclic-S—, $(C_2-C_{20})$ alkenyl-S—, $(C_3-C_{20})$cycloalkenyl-S—, $(C_2-C_{20})$alkynyl-S—, $(C_5-C_{20})$cycloalkynyl-S—, $(C_5-C_{25})$aryl-S—, perhalo$(C_1-C_{20})$alkyl-S—, $(C_1-C_{20})$alkyl-SO$_2$—, phenyl-SO$_2$—, $(C_3-C_{20})$cycloalkyl-SO$_2$—, $(C_1-C_{20})$alkoxy-SO$_2$—, $(C_3-C_{25})$heteroaryl-SO$_2$—, $(C_3-C_{25})$heterocyclic-SO$_2$—, $(C_2-C_{20})$alkenyl-SO$_2$—, $(C_3-C_{20})$cycloalkenyl-SO$_2$—, $(C_2-C_{20})$alkynyl-SO$_2$—, $(C_5-C_{20})$cycloalkynyl-SO$_2$—, $(C_5-C_{25})$aryl-SO$_2$—, perhalo$(C_1-C_{20})$alkyl-SO$_2$—, H$_2$N—SO$_2$—, $(C_1-C_{20})$alkyl-NH—SO$_2$—, phenyl-NH—SO$_2$—, $(C_3-C_{20})$cycloalkyl-NH—SO$_2$—, $(C_1-C_{20})$alkoxy-NH—SO$_2$—, $(C_3-C_{25})$heteroaryl-NH—SO$_2$—, $(C_3-C_{25})$heterocyclic-NH—SO$_2$—, $(C_2-C_{20})$alkenyl-NH—SO$_2$—, $(C_3-C_{20})$cycloalkenyl-NH—SO$_2$—, $(C_2-C_{20})$alkynyl-NH—SO$_2$—, $(C_5-C_{20})$cycloalkynyl-NH—SO$_2$—, $(C_5-C_{25})$aryl-NH—SO$_2$—, perhalo$(C_1-C_{20})$alkyl-NH—SO$_2$—, $\{(C_1-C_{20})$alkyl$\}_2$N—SO$_2$—, $\{$phenyl$\}_2$N—SO$_2$—, $\{(C_3-C_{20})$cycloalkyl$\}_2$N—SO$_2$—, $\{(C_1-C_{20})$alkoxy$\}_2$N—SO$_2$—, $\{(C_3-C_{25})$heteroaryl$\}_2$N—SO$_2$—, $\{(C_3-C_{25})$heterocyclic$\}_2$N—SO$_2$—, $\{(C_2-C_{20})$alkenyl$\}_2$N—SO$_2$—, $\{(C_2-C_{20})$alkynyl$\}_2$N—SO$_2$—, $\{(C_5-C_{20})$cycloalkynyl$\}_2$N—SO$_2$—, $\{(C_5-C_{25})$aryl$\}_2$N—SO$_2$—, $\{$perhalo$(C_1-C_{20})$alkyl$\}_2$N—SO$_2$—, $(C_1-C_{20})$alkyl-SO$_2$—NH—, phenyl-SO$_2$—NH—, $(C_3-C_{20})$cycloalkyl-SO$_2$—NH—, $(C_1-C_{20})$alkoxy-SO$_2$—NH—, $(C_3-C_{25})$heteroaryl-SO$_2$—NH—, $(C_3-C_{25})$heterocyclic-SO$_2$—NH—, $(C_2-C_{20})$alkenyl-SO$_2$—NH—, $(C_3-C_{20})$cycloalkenyl-SO$_2$—NH—, $(C_2-C_{20})$alkynyl-SO$_2$—NH—, $(C_5-C_{20})$cycloalkynyl-SO$_2$—NH—, $(C_5-C_{25})$aryl-SO$_2$—NH—, perhalo$(C_1-C_{20})$alkyl-SO$_2$—NH—, $(C_1-C_{20})$alkyl-NH—, phenyl-NH—, $(C_3-C_{20})$cycloalkyl-NH—, $(C_1-C_{20})$alkoxy-NH—, $(C_3-C_{25})$heteroaryl-NH—, $(C_3-C_{25})$heterocyclic-NH—, $(C_2-C_{20})$alkenyl-NH—, $(C_3-C_{20})$cycloalkenyl-NH—, $(C_2-C_{20})$alkynyl-NH—, $(C_5-C_{20})$cycloalkynyl-NH—, $(C_5-C_{25})$aryl-NH—, perhalo$(C_1-C_{20})$alkyl-NH—, $\{(C_1-C_{20})$alkyl$\}_2$N—, $\{$phenyl$\}_2$N—, $\{(C_3-C_{20})$cycloalkyl$\}_2$N—, $\{(C_1-C_{20})$alkoxy$\}_2$N—, $\{(C_3-C_{25})$heteroaryl$\}_2$N—, $\{(C_3-C_{25})$heterocyclic$\}_2$N—, $(C_2-C_{20})$alkenyl$\}_2$N—, $\{(C_3-C_{20})$cycloalkenyl$\}_2$N—, $\{(C_2-C_{20})$alkynyl$\}_2$N—, $\{(C_5-C_{20})$cycloalkynyl$\}_2$N—, $\{(C_5-C_{25})$aryl$\}_2$N—, $\{$perhalo$(C_1-C_{20})$alkyl$\}_2$N—, $(C_1-C_{20})$alkyl-(C=O)—NH—, phenyl-(C=O)—NH—, $(C_3-C_{20})$cycloalkyl-(C=O)—NH—, $(C_1-C_{20})$alkoxy-(C=O)—NH—, $(C_3-C_{25})$heteroaryl-(C=O)—NH—, $(C_3-C_{25})$heterocyclic-(C=O)—NH—, $(C_2-C_{20})$alkenyl-(C=O)—NH—, $(C_3-C_{20})$cycloalkenyl-(C=O)—NH—, $(C_2-C_{20})$alkynyl-(C=O)—NH—, $(C_5-C_{25})$aryl-(C=O)—NH—, perhalo$(C_1-C_{20})$alkyl-(C=O)—NH—, $(C_1-C_{20})$alkyl-(C=O)$\{((C_1-C_{20})$alkyl)N$\}$—, phenyl-(C=O)$\{((C_1-C_{20})$alkyl)N$\}$—, $(C_3-C_{20})$cycloalkyl-(C=O)—$\{((C_1-C_{20})$alkyl)N$\}$—, $(C_1-C_{20})$alkoxy-(C=O)—$\{((C_1-C_{20})$alkyl)N$\}$—, $(C_3-C_{25})$heteroaryl-(C=O)—$\{((C_1-C_{20})$alkyl)N$\}$—, $(C_3-C_{25})$heterocyclic-(C=O)—$\{((C_1-C_{20})$alkyl)N$\}$—, $(C_2-C_{20})$alkenyl-(C=O)—$\{((C_1-C_{20})$alkyl)N$\}$—, $(C_3-C_{20})$cycloalkenyl-(C=O)$\{((C_1-C_{20})$alkyl)N$\}$—, $(C_2-C_{20})$alkynyl-(C=O)$\{((C_1-C_{20})$alkyl)N$\}$—, $(C_5-C_{20})$cycloalkynyl-(C=O)—$\{((C_1-C_{20})$alkyl)N$\}$—, $(C_5-C_{25})$aryl-(C=O)—$\{((C_1-C_{20})$alkyl)N$\}$—, perhalo$(C_1-C_{20})$alkyl-(C=O)—$\{((C_1-C_{20})$alkyl)N$\}$—, phenyl-(C=O)—NH—, phenyl-(C=O)-$\{($phenyl$)$N$\}$—, $(C_1-C_{20})$alkyl-(C=O)$\{($phenyl$)$N$\}$—, $(C_3-C_{20})$cycloalkyl-(C=O)-$\{($phenyl$)$N$\}$—, $(C_1-C_{20})$alkoxy-(C=O)-$\{($phenyl$)$N$\}$—, $(C_3-C_{25})$heteroaryl-(C=O)-$\{($phenyl$)$N$\}$—, $(C_3-C_{25})$heterocyclic-(C=O)-$\{($phenyl$)$N$\}$—, $(C_2-C_{20})$alkenyl-(C=O#$\{($phenyl$)$N$\}$—, $(C_3-C_{20})$cycloalkenyl-(C=O)-$\{($phenyl$)$N$\}$—, $(C_2-C_{20})$alkynyl-(C=O)-$\{($phenyl$)$N$\}$—, $(C_5-C_{20})$cycloalkynyl-(C=O)-$\{($phenyl$)$N$\}$—, $(C_5-C_{25})$aryl-(C=O)—$\{($phenyl$)$N$\}$—, perhalo$(C_1-C_{20})$alkyl-(C=O)-$\{($phenyl$)$N$\}$—, H$_2$N—(C=O)—, $(C_1-C_{20})$alkyl-NH—(C=O)—, phenyl-NH—(C=O)—, $(C_3-C_{20})$cycloalkyl-NH—(C=O)—, $(C_1-C_{20})$alkoxy-NH—(C=O)—, $(C_3-C_{25})$heteroaryl-NH—(C=O)—, $(C_3-C_{25})$heterocyclic-NH—(C=O)—, $(C_2-C_{20})$alkenyl-NH—(C=O)—, $(C_3-C_{20})$cycloalkenyl-NH—(C=O)—, $(C_2-C_{20})$alkynyl-NH—(C=O)—, $(C_5-C_{20})$cycloalkynyl-NH—(C=O)—, $(C_5-C_{25})$aryl-NH—(C=O)—, perhalo$(C_1-C_{20})$alkyl-NH—(C=O)—, $\{(C_1-C_{20})$alkyl$\}_2$N—(C=O)—, $\{$phenyl$\}\{(C_1-C_{20})$alkyl$\}$N—(C=O)—, $\{(C_3-C_{20})$cycloalkyl$\}\{(C_1-C_{20})$alkyl$\}$N—(C=O)—, $\{(C_1-C_{20})$alkoxy$\}\{(C_1-C_{20})$alkyl$\}$N—(C=O)—, $\{(C_3-C_{25})$heteroaryl$\}\{(C_1-C_{20})$alkyl$\}$N—(C=O)—, $\{(C_3-C_{25})$heterocyclic$\}\{(C_1-C_{20})$alkyl$\}$N—(C=O)—, $\{(C_2-C_{20})$alkenyl$\}\{(C_1-C_{20})$alkyl$\}$N—(C=O)—, $\{(C_3-C_{20})$cycloalkenyl$\}\{(C_1-C_{20})$alkyl$\}$N—(C=O)—, $\{(C_2-C_{20})$alkynyl$\}\{(C_1-C_{20})$alkyl$\}$N—(C=O)—, $\{(C_5-C_{20})$cycloalkynyl$\}\{(C_1-C_{20})$alkyl$\}$N—(C=O)—, $\{(C_5-C_{25})$aryl$\}\{(C_1-C_{20})$alkyl$\}$N—(C=O)—, $\{$perhalo$(C_1-C_{20})$alkyl$\}\{(C_1-C_{20})$alkyl$\}$N—(C=O)—, $\{$phenyl$\}_2$N—(C=O)—, $\{(C_3-C_{20})$cycloalkyl$\}\{$phenyl$\}$N—(C=O)—, $\{(C_1-C_{20})$alkoxy$\}\{$phenyl$\})$N—(C=O)—, $\{(C_3-C_{25})$heteroaryl$\}\{$phenyl$\}$N—(C=O)—, $\{(C_3-C_{25})$heterocyclic$\}\{$phenyl$\}$N—(C=O)—, $\{(C_2-C_{20})$alkenyl$\}\{$phenyl$\}$N—(C=O)—, $\{(C_3-C_{20})$cycloalkenyl$\}\{$phenyl$\}$N—(C=O)—, $\{(C_2-C_{20})$alkynyl$\}\{$phenyl$\}$N—(C=O)—, $\{(C_5-C_{20})$cycloalkynyl$\}\{$phenyl$\}$N—(C=O)—, $\{(C_5-C_{25})$aryl$\}\{$phenyl$\}$N—(C=O)—, $\{$perhalo$(C_1-C_{20})$alkyl$\}\{$phenyl$\}$N—(C=O)—, HO—(C=O)—, $(C_1-C_{20})$alkyl-(C=O)—, $(C_3-C_{25})$heteroaryl-(C=O)—, $(C_3-C_{25})$heterocyclic-(C=O)—, $(C_2-C_{20})$alkenyl-(C=O)—, $(C_3-C_{20})$cycloalkenyl-(C=O)—, $(C_2-C_{20})$alkynyl-(C=O)—, $(C_5-C_{25})$aryl-(C=O)—, perhalo$(C_1-C_{20})$alkyl-(C=O)—, phenyl-(C=O)—, $(C_1-C_{20})$alkyl-O—(C=O)—, $(C_3-C_{25})$heteroaryl-O—(C=O)—, $(C_3-C_{25})$heterocyclic-O—(C=O)—, $(C_2-C_{20})$alkenyl-O—(C=O)—, $(C_3-C_{20})$cycloalkenyl-O—(C=O)—, $(C_2-C_{20})$alkynyl-O—(C=O)—, $(C_5-C_{25})$aryl-O—(C=O), perhalo$(C_1-C_{20})$alkyl-O—(C=O)—, phenyl-O—(C=O)—, $(C_1-C_{20})$alkyl-(C=O)—O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-C_{20})$cycloalkenyl-(C=O)—O—, $(C_2-C_{20})$alkynyl-(C=O)—O—, $(C_5-C_{25})$aryl-(C=O)—O—, phenyl-(C=O)—O—, perhalo$(C_1-C_{20})$alkyl-(C=O)—O—, and salts thereof; and wherein R$^2$, R$^3$, R$^4$, R$^5$, R$^6$, R$^7$, R$^8$, R$^9$, R$^{10}$, and R$^{11}$ are each independently selected from the group consisting of hydrogen, hydroxy, halo, bromo, chloro, iodo, fluoro, —N$_3$, —CN, —NC, —SH, —NO$_2$, —NH$_2$, $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, $(C_5-C_{25})$aryl, perhalo$(C_1-C_{20})$alkyl, $(C_1-C_{20})$alkyl-O—, phenyl-O—, $(C_3-C_{20})$cycloalkyl-O—, $(C_3-C_{25})$heteroaryl-O—, $(C_3-C_{25})$heterocyclic-O—, $(C_2-C_{20})$alkenyl-O—, $(C_3-C_{20})$cycloalkenyl-O—, $(C_2-C_{20})$alkynyl-O—, $(C_5-C_{20})$cycloalkynyl-O—, $(C_5-C_{25})$aryl-O—, perhalo$(C_1-C_{20})$alkyl-O—, $(C_1-C_{20})$alkyl-S—, phenyl-S—, $(C_3-C_{20})$cycloalkyl-S—, $(C_3-C_{25})$heteroaryl-S—, $(C_3-C_{25})$heterocyclic-S—, $(C_2-C_{20})$alkenyl-S—, $(C_3-C_{20})$cycloalkenyl-S—, $(C_2-C_{20})$alkynyl-S—, $(C_5-C_{20})$cycloalkynyl-S—, $(C_5-C_{25})$aryl-S—, perhalo$(C_1-C_{20})$alkyl-S—, $(C_1-C_{20})$alkyl-SO$_2$—, phenyl-SO$_2$—, $(C_3-C_{20})$cycloalkyl-SO$_2$—, $(C_1-C_{20})$alkoxy-SO$_2$—, $(C_3-C_{25})$heteroaryl-SO$_2$—, $(C_3-C_{25})$heterocyclic-SO$_2$—, $(C_2-C_{20})$alkenyl-SO$_2$—, $(C_3-C_{20})$cycloalkenyl-SO$_2$—, $(C_2-C_{20})$alkynyl-SO$_2$—, $(C_5-C_{20})$cycloalkynyl-SO$_2$—, $(C_5-C_{25})$aryl- SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-C$_{25}$)heteroaryl-NH—SO$_2$—, (C$_3$-C$_{25}$)heterocyclic-NH—SO$_2$—, (C$_2$-C$_{20}$)alkenyl-NH—SO$_2$—, (C$_3$-C$_{20}$)cycloalkenyl-NH—SO$_2$—, (C$_2$-C$_{20}$)alkynyl-NH—SO$_2$—, (C$_5$-C$_{20}$)cycloalkynyl-NH—SO$_2$—, (C$_5$-C$_{25}$)aryl-NH—SO$_2$—, perhalo(C$_1$-C$_{20}$)alkyl-NH—SO$_2$—, {(C$_1$-C$_{20}$)alkyl}$_2$N—SO$_2$—, {phenyl}$_2$N—SO$_2$—, {(C$_3$-C$_{20}$)cycloalkyl}$_2$N—SO$_2$—, {(C$_1$-C$_{20}$)alkoxy}$_2$N—SO$_2$—, {(C$_3$-C$_{25}$)heteroaryl}$_2$N—SO$_2$—, {(C$_3$-C$_{25}$)heterocyclic}$_2$N—SO$_2$—, {(C$_2$-C$_{20}$)alkenyl}$_2$N—SO$_2$—, {(C$_2$-C$_{20}$)alkynyl}$_2$N—SO$_2$—, {(C$_5$-C$_{20}$)cycloalkynyl}$_2$N—SO$_2$—, {(C$_5$-C$_{25}$)aryl}$_2$N—SO$_2$—, {perhalo(C$_1$-C$_{20}$)alkyl}$_2$N—SO$_2$—, (C$_1$-C$_{20}$)alkyl-SO$_2$—NH—, phenyl-SO$_2$—NH—, (C$_3$-C$_{20}$)cycloalkyl-SO$_2$—NH—, (C$_1$-C$_{20}$)alkoxy-SO$_2$—NH—, (C$_3$-C$_{25}$)heteroaryl-SO$_2$—NH—, (C$_3$-C$_{25}$)heterocyclic-SO$_2$—NH—, (C$_2$-C$_{20}$)alkenyl-SO$_2$—NH—, (C$_3$-C$_{20}$)cycloalkenyl-SO$_2$—NH—, (C$_2$-C$_{20}$)alkynyl-SO$_2$—NH—, (C$_5$-C$_{20}$)cycloalkynyl-SO$_2$—NH—, (C$_5$-C$_{25}$)aryl-SO$_2$—NH—, perhalo(C$_1$-C$_{20}$)alkyl-SO$_2$—NH—, (C$_1$-C$_{20}$)alkyl-NH—, phenyl-NH—, (C$_3$-C$_{20}$)cycloalkyl-NH—, (C$_1$-C$_{20}$)alkoxy-NH—, (C$_3$-C$_{25}$)heteroaryl-NH—, (C$_3$-C$_{25}$)heterocyclic-NH—, (C$_2$-C$_{20}$)alkenyl-NH—, (C$_3$-C$_{20}$)cycloalkenyl-NH—, (C$_2$-C$_{20}$)alkynyl-NH—, (C$_5$-C$_{20}$)cycloalkynyl-NH—, (C$_5$-C$_{25}$)aryl-NH—, perhalo(C$_1$-C$_{20}$)alkyl-NH—, {(C$_1$-C$_{20}$)alkyl}$_2$N—, {phenyl}$_2$N—, {(C$_3$-C$_{20}$)cycloalkyl}$_2$N—, {(C$_1$-C$_{20}$)alkoxy}$_2$N—, {(C$_3$-C$_{25}$)heteroaryl}$_2$N—, {(C$_3$-C$_{25}$)heterocyclic}$_2$N—, {(C$_2$-C$_{20}$)alkenyl}$_2$N—, {(C$_3$-C$_{20}$)cycloalkenyl}$_2$N—, {(C$_2$-C$_{20}$)alkynyl}$_2$N—, {(C$_5$-C$_{20}$)cycloalkynyl}$_2$N—, {(C$_5$-C$_{25}$)aryl}$_2$N—, {perhalo(C$_1$-C$_{20}$)alkyl}$_2$N—, (C$_1$-C$_{20}$)alkyl-(C=O)—NH—, phenyl-(C=O)—NH—, (C$_3$-C$_{20}$)cycloalkyl-(C=O)—NH—, (C$_1$-C$_{20}$)alkoxy-(C=O)—NH—, (C$_3$-C$_{25}$)heteroaryl-(C=O)—NH—, (C$_3$-C$_{25}$)heterocyclic-(C=O)NH—, (C$_2$-C$_{20}$)alkenyl-(C=O)NH—, (C$_3$-C$_{20}$)cycloalkenyl-(C=O)NH—, (C$_2$-C$_{20}$)alkynyl-(C=O)NH—, (C$_5$-C$_{20}$)cycloalkynyl-(C=O)—NH—, (C$_5$-C$_{25}$)aryl-(C=O)—NH—, perhalo(C$_1$-C$_{20}$)alkyl-(C=O)NH—, (C$_1$-C$_{20}$)alkyl-(C=O){((C$_1$-C$_{20}$)alkyl)N}—, phenyl-(C=O)—{((C$_1$-C$_{20}$)alkyl)N}—, (C$_3$-C$_{20}$)cycloalkyl-(C=O)—{((C$_1$-C$_{20}$)alkyl)N}—, (C$_1$-C$_{20}$)alkoxy-(C=O)—{((C$_1$-C$_{20}$)alkyl)N}—, (C$_3$-C$_{25}$)heteroaryl-(C=O)-{((C$_1$-C$_{20}$)alkyl)N}—, (C$_3$-C$_{25}$)heterocyclic-(C=O)—{((C$_1$-C$_{20}$)alkyl)N}—, (C$_2$-C$_{20}$)alkenyl-(C=O){((C$_1$-C$_{20}$)alkyl)N}—, (C$_3$-C$_{20}$)cycloalkenyl-(C=O)—{((C$_1$-C$_{20}$)alkyl)N}—, (C$_2$-C$_{20}$)alkynyl-(C=O){((C$_1$-C$_{20}$)alkyl)N}—, (C$_5$-C$_{20}$)cycloalkynyl-(C=O)—{((C$_1$-C$_{20}$)alkyl)N}—, (C$_5$-C$_{25}$)aryl-(C=O){((C$_1$-C$_{20}$)alkyl)N}—, perhalo(C$_1$-C$_{20}$)alkyl-(C=O){((C$_1$-C$_{20}$)alkyl)N}—, phenyl-(C=O)—NH—, phenyl-(C=O){(phenyl)N}—, (C$_1$-C$_{20}$)alkyl-(C=O)-{(phenyl)N}—, (C$_3$-C$_{20}$)cycloalkyl-(C=O)-{(phenyl)N}—, (C$_1$-C$_{20}$)alkoxy-(C=O)-{(phenyl)N}—, (C$_3$-C$_{25}$)heteroaryl-(C=O)-{(phenyl)N}—, (C$_3$-C$_{25}$)heterocyclic-(C=O)-{(phenyl)N}—, (C$_2$-C$_{20}$)alkenyl-(C=O)-{(phenyl)N}—, (C$_3$-C$_{20}$)cycloalkenyl-(C=O)-{(phenyl)N}—, (C$_2$-C$_{20}$)alkynyl-(C=O){(phenyl)N}—, (C$_5$-C$_{20}$)cycloalkynyl-(C=O)-{(phenyl)N}—, (C$_5$-C$_{25}$)aryl-(C=O)-{(phenyl)N}—, perhalo(C$_1$-C$_{20}$)alkyl-(C=O)-{(phenyl)N}—, H$_2$N(C=O)—, (C$_1$-C$_{20}$)alkyl-NH—(C=O)—, phenyl-NH—(C=O)—, (C$_3$-C$_{20}$)cycloalkyl-NH—(C=O)—, (C$_1$-C$_{20}$)alkoxy-NH—(C=O), (C$_3$-C$_{25}$)heteroaryl-NH—(C=O)—, (C$_3$-C$_{25}$)heterocyclic-NH—(C=O)—, (C$_2$-C$_{20}$)alkenyl-NH—(C=O)—, (C$_3$-C$_{20}$)cycloalkenyl-NH—(C=O)—, (C$_2$-C$_{20}$)alkynyl-NH—(C=O)—, (C$_5$-C$_{20}$)cycloalkynyl-NH—(C=O)—, (C$_5$-C$_{25}$)aryl-NH—(C=O)—, perhalo(C$_1$-C$_{20}$)alkyl-NH—(C=O)—, {(C$_1$-C$_{20}$)alkyl}$_2$N—(C=O)—, {phenyl}{((C$_1$-C$_{20}$)alkyl}N—(C=O)—, {(C$_3$-C$_{20}$)cycloalkyl}{((C$_1$-C$_{20}$)alkyl}N—(C=O)—, {(C$_1$-C$_{20}$)alkoxy}{(C$_1$-C$_{20}$)alkyl}N—(C=O)—, {(C$_3$-C$_{25}$)heteroaryl}{(C$_1$-C$_{20}$)alkyl}-(C=O)—, {(C$_3$-C$_{25}$)heterocyclic}{(C$_1$-C$_{20}$)alkyl}N—(C=O)—, {(C$_2$-C$_{20}$)alkenyl}{(C$_1$-C$_{20}$)alkyl}N—(C=O)—, {(C$_3$-C$_{20}$)cycloalkenyl}{(C$_1$-C$_{20}$)alkyl)}N—(C=O)—, {(C$_2$-C$_{20}$)alkynyl}{(C$_1$-C$_{20}$)alkyl}N—(C=O)—, {(C$_5$-C$_{20}$)cycloalkynyl}{(C$_1$-C$_{20}$)alkyl}N—(C=O)—, {(C$_5$-C$_{25}$)aryl}{(C$_1$-C$_{20}$)alkyl}N—(C=O)—, {perhalo(C$_1$-C$_{20}$)alkyl}{(C$_1$-C$_{20}$)alkyl}N+C=O)—, {phenyl}$_2$N—(C=O)—, {(C$_3$-C$_{20}$)cycloalkyl}{phenyl}N—(C=O)—, {(C$_1$-C$_{20}$)alkoxy}{phenyl}N—(C=O)—, {(C$_3$-C$_{25}$)heteroaryl}{phenyl}N—(C=O)—, {(C$_3$-C$_{25}$)heterocyclic}{phenyl}N—(C=O)—, {(C$_2$-C$_{20}$)alkenyl}{phenyl}N—(C=O)—, {(C$_3$-C$_{20}$)cycloalkenyl}{phenyl}N—(C=O)—, {(C$_2$-C$_{20}$)alkynyl}{phenyl}N—(C=O)—, {(C$_5$-C$_{20}$)cycloalkynyl}{phenyl}N—(C=O)—, {(C$_5$-C$_{25}$)aryl}{phenyl}N—(C=O)—, {perhalo(C$_1$-C$_{20}$)alkyl}{phenyl}N—(C=O)—, HO—(C=O)—, (C$_1$-C$_{20}$)alkyl-(C=O)—, (C$_3$-C$_{25}$)heteroaryl-(C=O)—, (C$_3$-C$_{25}$)heterocyclic-(C=O)—, (C$_2$-C$_{20}$)alkenyl-(C=O)—, (C$_3$-C$_{20}$)cycloalkenyl-(C=O)—, (C$_2$-C$_{20}$)alkynyl-(C=O)—, (C$_5$-C$_{25}$)aryl-(C=O)—, perhalo(C$_1$-C$_{20}$)alkyl-(C=O)—, phenyl-(C=O)—, (C$_1$-C$_{20}$)alkyl-O—(C=O)—, (C$_3$-C$_{25}$)heteroaryl-O—(C=O)—, (C$_3$-C$_{25}$)heterocyclic-O—(C=O)—, (C$_2$-C$_{20}$)alkenyl-O—(C=O)—, (C$_3$-C$_{20}$)cycloalkenyl-O—(C=O)—, (C$_2$-C$_{20}$)alkynyl-O—(C=O)—, (C$_5$-C$_{25}$)aryl-O—(C=O)—, perhalo(C$_1$-C$_{20}$)alkyl-O—(C=O)—, phenyl-O—(C=O)—, (C$_1$-C$_{20}$)alkyl-(C=O)—O—, (C$_3$-C$_{25}$)heteroaryl-(C=O)—O—, (C$_3$-C$_{25}$)heterocyclic-(C=O)—O—, (C$_2$-C$_{20}$)alkenyl-(C=O)—O—, (C$_3$-C$_{20}$)cycloalkenyl-(C=O)—O—, (C$_2$-C$_{20}$)alkynyl-(C=O)—O—, (C$_5$-C$_{25}$)aryl-(C=O)—O—, phenyl-(C=O)—O—, perhalo(C$_1$-C$_{20}$)alkyl-(C=O)—O—, and salts thereof;

wherein each of the aforesaid (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, and (C$_5$-C$_{25}$)aryl groups (for said R$^2$, R$^3$, R$^4$, R$^5$, R$^6$, R$^7$, R$^8$, R$^9$, R$^{10}$, and R$^{11}$ groups) may be optionally and independently substituted by one to four moieties selected from the group consisting of hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, (C$_5$-C$_{25}$)aryl-SO$_2$—, perhalo(C$_1$-C$_{20}$)alkyl-SO$_2$—, H$_2$N—SO$_2$—, (C$_1$-C$_{20}$)alkyl-NH—SO$_2$—, phenyl-NH—SO$_2$—, (C$_3$-C$_{20}$)cycloalkyl-NH—SO$_2$—, (C$_1$-C$_{20}$)alkoxy-NH—SO$_2$—, (C$_3$-

$C_{25}$)heteroaryl-NH—$SO_2$—, ($C_3$-$C_{25}$)heterocyclic-NH—$SO_2$—, ($C_2$-$C_{20}$)alkenyl-NH—$SO_2$—, ($C_3$-$C_{20}$)cycloalkenyl-NH—$SO_2$—, ($C_2$-$C_{20}$)alkynyl-NH—$SO_2$—, ($C_5$-$C_{20}$)cycloalkynyl-NH—$SO_2$—, ($C_5$-$C_{25}$)aryl-NH—$SO_2$—, perhalo($C_1$-$C_{20}$)alkyl-NH—$SO_2$—, {($C_1$-$C_{20}$)alkyl}$_2$N—$SO_2$—, {phenyl}$_2$N—$SO_2$—, {($C_3$-$C_{20}$)cycloalkyl}$_2$N—$SO_2$—, {($C_1$-$C_{20}$)alkoxy}$_2$N—$SO_2$—, {($C_3$-$C_{25}$)heteroaryl}$_2$N—$SO_2$—, {($C_3$-$C_{25}$)heterocyclic}$_2$N—$SO_2$—, {($C_2$-$C_{20}$)alkenyl}$_2$N—$SO_2$—, {($C_2$-$C_{20}$)alkynyl}$_2$N—$SO_2$—, {($C_5$-$C_{20}$)cycloalkynyl}$_2$N—$SO_2$—, {($C_5$-$C_{25}$)aryl}$_2$N—$SO_2$—, {perhalo($C_1$-$C_{20}$)alkyl}$_2$N—$SO_2$—, ($C_1$-$C_{20}$)alkyl-$SO_2$—NH—, phenyl-$SO_2$—NH—, ($C_3$-$C_{20}$)cycloalkyl-$SO_2$—NH—, ($C_1$-$C_{20}$)alkoxy-$SO_2$—NH—, ($C_3$-$C_{25}$)heteroaryl-$SO_2$—NH—, ($C_3$-$C_{25}$)heterocyclic-$SO_2$—NH—, ($C_2$-$C_{20}$)alkenyl-$SO_2$—NH—, ($C_3$-$C_{20}$)cycloalkenyl-$SO_2$—NH—, ($C_2$-$C_{20}$)alkynyl-$SO_2$—NH—, ($C_5$-$C_{20}$)cycloalkynyl-$SO_2$—N—, ($C_5$-$C_{25}$)aryl-$SO_2$—NH—, perhalo($C_1$-$C_{20}$)alkyl-$SO_2$—NH—, ($C_1$-$C_{20}$)alkyl-NH—, phenyl-NH—, ($C_3$-$C_{20}$)cycloalkyl-NH—, ($C_1$-$C_{20}$)alkoxy-NH—, ($C_3$-$C_{25}$)heteroaryl-NH—, ($C_3$-$C_{25}$)heterocyclic-NH—, ($C_2$-$C_{20}$)alkenyl-NH—, ($C_3$-$C_{20}$)cycloalkenyl-NH—, ($C_2$-$C_{20}$)alkynyl-NH—, ($C_5$-$C_{20}$)cycloalkynyl-NH—, ($C_5$-$C_{25}$)aryl-NH—, perhalo($C_1$-$C_{20}$)alkyl-NH—, {($C_1$-$C_{20}$)alkyl}$_2$N—, {phenyl}$_2$N—, {($C_3$-$C_{20}$)cycloalkyl}$_2$N—, {($C_1$-$C_{20}$)alkoxy}$_2$N—, {($C_3$-$C_{25}$)heteroaryl}$_2$N—, {($C_3$-$C_{25}$)heterocyclic}$_2$N—, {($C_2$-$C_{20}$)alkenyl}$_2$N—, {($C_3$-$C_{20}$)cycloalkenyl}$_2$N—, {($C_2$-$C_{20}$)alkynyl}$_2$N—, {($C_5$-$C_{20}$)cycloalkynyl}$_2$N—, {($C_5$-$C_{25}$)aryl}$_2$N—, {perhalo($C_1$-$C_{20}$)alkyl}$_2$N—, ($C_1$-$C_{20}$)alkyl-(C=O)—NH—, phenyl-(C=O)—NH—, ($C_3$-$C_{20}$)cycloalkyl-(C=O)—NH—, ($C_1$-$C_{20}$)alkoxy-(C=O)—NH—, ($C_3$-$C_{25}$)heteroaryl-(C=O)—NH—, ($C_3$-$C_{25}$)heterocyclic-(C=O)—NH—, ($C_2$-$C_{20}$)alkenyl-(C=O)—NH—, ($C_3$-$C_{20}$)cycloalkenyl-(C=O)—NH—, ($C_2$-$C_{20}$)alkynyl-(C=O)—NH—, ($C_5$-$C_{20}$)cycloalkynyl-(C=O)—NH—, ($C_5$-$C_{25}$)aryl-(C=O)—NH—, perhalo($C_1$-$C_{20}$)alkyl-(C=O)—NH—, ($C_1$-$C_{20}$)alkyl-(C=O)—{(($C_1$-$C_{20}$)alkyl)N}—, phenyl-(C=O)—{(($C_1$-$C_{20}$)alkyl)N}—, ($C_3$-$C_{20}$)cycloalkyl-(C=O)—{(($C_1$-$C_{20}$)alkyl)N}—, ($C_1$-$C_{20}$)alkoxy-(C=O){(($C_1$-$C_{20}$)alkyl)N}—, ($C_3$-$C_{25}$)heteroaryl-(C=O)—{(($C_1$-$C_{20}$)alkyl)N}—, ($C_3$-$C_{25}$)heterocyclic-(C=O)—{(($C_1$-$C_{20}$)alkyl)N}—, ($C_2$-$C_{20}$)alkenyl-(C=O)—{(($C_1$-$C_{20}$)alkyl)N}—, ($C_3$-$C_{20}$)cycloalkenyl-(C=O#{(($C_1$-$C_{20}$)alkyl)N}—, ($C_2$-$C_{20}$)alkynyl-(C=O)—{(($C_1$-$C_{20}$)alkyl)N}—, ($C_5$-$C_{20}$)cycloalkynyl-(C=O)—{(($C_1$-$C_{20}$)alkyl)N}—, ($C_5$-$C_{25}$)aryl-(C=O)—{(($C_1$-$C_{20}$)alkyl)N}—, perhalo($C_1$-$C_{20}$)alkyl-(C=O){(($C_1$-$C_{20}$)alkyl)N}—, phenyl-(C=O)—NH—, phenyl-(C=O)-{(phenyl)N}—, ($C_1$-$C_{20}$)alkyl-(C=O)-{(phenyl)N}—, ($C_3$-$C_{20}$)cycloalkyl-(C=O)-{(phenyl)N}—, ($C_1$-$C_{20}$)alkoxy-(C=O)-{(phenyl)N}—, ($C_3$-$C_{25}$)heteroaryl-(C=O)-{(phenyl)N}—, ($C_3$-$C_{25}$)heterocyclic-(C=O)-{(phenyl)N}—, ($C_2$-$C_{20}$)alkenyl-(C=O)-{(phenyl)N}—, ($C_3$-$C_{20}$)cycloalkenyl-(C=O)-{(phenyl)N}—, ($C_2$-$C_{20}$)alkynyl-(C=O)-{(phenyl)N}—, ($C_5$-$C_{20}$)cycloalkynyl-(C=O)-{(phenyl)N}—, ($C_5$-$C_{25}$)aryl-(C=O){(phenyl)N}—, perhalo($C_1$-$C_{20}$)alkyl-(C=O)-{(phenyl)N}—, $H_2$N(C=O)—, ($C_1$-$C_{20}$)alkyl-NH—(C=O)—, phenyl-NH—(C=O)—, ($C_3$-$C_{20}$)cycloalkyl-NH—(C=O)—, ($C_1$-$C_{20}$)alkoxy-NH—(C=O), ($C_3$-$C_{25}$)heteroaryl-NH—(C=O)—, ($C_3$-$C_{25}$)heterocyclic-NH—(C=O)—, ($C_2$-$C_{20}$)alkenyl-NH—(C=O)—, ($C_3$-$C_{20}$)cycloalkenyl-NH—(C=O)—, ($C_2$-$C_{20}$)alkynyl-NH—(C=O)—, ($C_5$-$C_{20}$)cycloalkynyl-NH—(C=O)—, ($C_5$-$C_{25}$)aryl-NH—(C=O)—, perhalo($C_1$-$C_{20}$)alkyl-NH—(C=O)—, {($C_1$-$C_{20}$)alkyl}$_2$N—(C=O)—, {phenyl}{($C_1$-$C_{20}$)alkyl}N—(C=O)—, —{($C_3$-$C_{25}$)cycloalkyl}{($C_1$-$C_{20}$)alkyl}N—(C=O)—, {($C_1$-$C_{20}$)alkoxy}{($C_1$-$C_{20}$)alkyl}N—(C=O), {($C_3$-$C_{25}$)heteroaryl}{($C_1$-$C_{20}$)alkyl}N—(C=O)—, {($C_3$-$C_{25}$)heterocyclic}{($C_1$-$C_{20}$)alkyl}N—(C=O)—, {($C_2$-$C_{20}$)alkenyl}{($C_1$-$C_{20}$)alkyl}N—(C=O)—, {($C_3$-$C_{20}$)cycloalkenyl}{($C_1$-$C_{20}$)alkyl}N—(C=O)—, {($C_2$-$C_{20}$)alkynyl}{($C_1$-$C_{20}$)alkyl}N—(C=O)—, {($C_5$-$C_{20}$)cycloalkynyl}{($C_1$-$C_{20}$)alkyl}N—(C=O)—, {($C_5$-$C_{25}$)aryl}{($C_1$-$C_{20}$)alkyl}N—(C=O)—, {perhalo($C_1$-$C_{20}$)alkyl}{($C_1$-$C_{20}$)alkyl}N—(C=O)—, {phenyl}$_2$N—(C=O)—, {($C_3$-$C_{20}$)cycloalkyl}{phenyl}N—(C=O)—, {($C_1$-$C_{20}$)alkoxy}{phenyl}N—(C=O)—, {($C_3$-$C_{25}$)heteroaryl}{phenyl}N—(C=O)—, {($C_3$-$C_{25}$)heterocyclic}{phenyl}N—(C=O)—, {($C_2$-$C_{20}$)alkenyl}{phenyl}N—(C=O)—, {($C_3$-$C_{20}$)cycloalkenyl}{phenyl}N—(C=O)—, {($C_2$-$C_{20}$)alkynyl}{phenyl}N—(C=O)—, {($C_5$-$C_{20}$)cycloalkynyl}{phenyl}N—(C=O)—, {($C_5$-$C_{25}$)aryl}{phenyl}N—(C=O)—, {perhalo($C_1$-$C_{20}$)alkyl}{phenyl}N—(C=O)—, HO—(C=O)—, ($C_1$-$C_{20}$)alkyl-(C=O)—, ($C_3$-$C_{25}$)heteroaryl-(C=O)—, ($C_3$-$C_{25}$)heterocyclic-(C=O)—, ($C_2$-$C_{20}$)alkenyl-(C=O)—, ($C_3$-$C_{20}$)cycloalkenyl-(C=O)—, ($C_2$-$C_{20}$)alkynyl-(C=O)—, ($C_1$-$C_{20}$)aryl-(C=O)—, perhalo($C_1$-$C_{20}$)alkyl-(C=O)—, phenyl-(C=O)—, ($C_1$-$C_{20}$)alkyl-O—(C=O)—, ($C_3$-$C_{25}$)heteroaryl-O—(C=O)—, ($C_3$-$C_{25}$)heterocyclic-O—(C=O)—, ($C_2$-$C_{20}$)alkenyl-O—(C=O)—, ($C_3$-$C_{20}$)cycloalkenyl-O—(C=O)—, ($C_2$-$C_{20}$)alkynyl-O—(C=O)—, ($C_5$-$C_{25}$)aryl-O—(C=O)—, perhalo($C_1$-$C_{20}$)alkyl-O—(C=O)—, phenyl-O—(C=O)—, ($C_1$-$C_{20}$)alkyl-(C=O)—O—, ($C_3$-$C_{25}$)heteroaryl-(C=O)—O—, ($C_3$-$C_{25}$)heterocyclic-(C=O)—O—, ($C_2$-$C_{20}$)alkenyl-(C=O)—O—, ($C_3$-$C_{20}$)cycloalkenyl-(C=O)—O—, ($C_2$-$C_{20}$)alkynyl-(C=O)—O—, ($C_5$-$C_{25}$)aryl-(C=O)—O—, phenyl-(C=O)—O—, perhalo($C_1$-$C_{20}$)alkyl-(C=O)—O—, and salts thereof;

and wherein two independently chosen $R^2$, $R^3$, $R^4$, $R^5$, $R^6$, $R^7$, $R^8$, $R^9$, $R^{10}$, and $R^{11}$ alkyl-containing groups may be taken together with any atom to which they are attached to form a three to forty membered cyclic, heterocyclic or heteroaryl ring.

In the present application, "Ghy" is a guanylhydrazone group; GhyCH— is $NH_2C$(=NH)—NH—N—CH—; and GhyCH$_3$— is $NH_2C$(=NH)—NH—N=CCH$_3$—.

In another embodiment, a pharmaceutical composition of the carboxylic acid salt of the guanylhydrazone compound together with a pharmaceutically acceptable diluent or carrier is provided.

The invention further provides a tablet formulation comprising the carboxylic acid salt of the guanylhydrazone compound in an admixture with excipients. One embodiment formulation includes the carboxylic acid salt of the guanylhydrazone compound, a compression aid such as microcrystalline cellulose, an additive to provide sheen to the table such as anhydrous dibasic calcium phosphate, a disintegrant such as sodium starch glycolate and a lubricant such as magnesium stearate.

In addition the invention provides a capsule formulation comprising the carboxylic acid salt of the guanylhydrazone compound in an admixture with excipients. A preferred formulation includes the salt, an inert diluent, a dried disintegrant and a lubricant as described above.

The invention further provides the carboxylic acid salt of the guanylhydrazone compound in sterile aqueous solution for parenteral administration. Preferably such solution contains from 10 to 40% by volume of propylene glycol and preferably also sufficient sodium chloride to avoid haemolysis, e.g. about 1% w/v. The invention also provides the carboxylic acid salt of the guanylhydrazone compound for use in treating diseases and conditions as described in the patents and patent application publications listed above.

The guanylhydrazone compounds and certain carboxylic acids in combination thereof in the present invention can exist in several tautomeric forms, and geometric isomers and mixtures thereof. All such tautomeric forms are included within the scope of the present invention. Tautomers exist as mixtures of tautomers in solution. In solid form, usually one tautomer predominates. Even though one tautomer may be described, the present invention includes all tautomers of the present compounds.

The salt structures formed can be in either mono, di, tri, tetra or other salt structures and combinations thereof. The present invention also includes atropisomers of the present invention. Atropisomers refer to compounds of the invention that can be separated into rotationally restricted isomers. The compounds of this invention may contain olefin-like double bonds. When such bonds are present, the compounds of the invention exist as cis and trans configurations and as mixtures thereof.

The present invention also includes isotopically-labeled acid compounds, which are identical to those recited above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, would be preferred in some circumstances. Isotopically labeled compounds of this invention and prodrugs thereof can generally be prepared by carrying out the procedures disclosed herein by substituting a readily available isotopically labeled reagent for a non-isotopically labeled reagent.

In other embodiments, the invention relates to a guanylhydrazone compound combined with one or more acids, such as carboxylic acid, or one or more anions, such as mesylate, to form a salt having a solubility in pure water of at least 0.001 mg/mL, more preferably 0.01 mg/mL, more preferably 0.1 mg/mL, more preferably 0.2 mg/mL, more preferably 0.3 mg/mL, more preferably 0.4 mg/mL, more preferably 0.5 mg/mL, more preferably 0.7 mg/mL, more preferably 1 mg/mL, more preferably 2 mg/mL, more preferably 3 mg/mL, more preferably 4 mg/mL, more preferably 5 mg/mL, more preferably 10 mg/mL, more preferably 20 mg/mL, even more preferably 30 mg/mL, still more preferably 40 mg/mL, yet still more preferably 50 mg/mL, more preferably 55 mg/mL, more preferably 75 mg/mL, more preferably 85 mg/mL, more preferably 100 mg/mL, more preferably 200 mg/mL, more preferably 300 mg/mL, more preferably 500 mg/mL and most preferably 1000 mg/mL.

In other embodiments, the invention relates to a guanylhydrazone compound combined with one or more acids or anions to form a salt having a solubility, in a 5% by weight dextrose aqueous solution with pure water, of at least 0.001 mg/mL, more preferably 0.01 mg/mL, more preferably 0.1 mg/mL, more preferably 0.2 mg/mL, more preferably 0.3 mg/mL, more preferably 0.4 mg/mL, more preferably 0.5 mg/mL, more preferably 0.7 mg/mL, more preferably 1 mg/mL, more preferably 2 mg/mL, more preferably 3 mg/mL, more preferably 4 mg/mL, more preferably 5 mg/mL, more preferably 10 mg/mL, more preferably 20 mg/mL, even more preferably 30 mg/mL, still more preferably 40 mg/mL, yet still more preferably 50 mg/mL, more preferably 55 mg/mL, more preferably 75 mg/mL, more preferably 85 mg/mL, more preferably 100 mg/mL, more preferably 200 mg/mL, more preferably 300 mg/mL, more preferably 500 mg/mL and most preferably 1000 mg/mL.

In other embodiments, the invention relates to a guanylhydrazone compound combined with one or more acids or anions to form a salt having a solubility, in both pure water and in a 5% by weight dextrose aqueous solution with pure water, of at least 0.001 mg/mL, more preferably 0.01 mg/mL, more preferably 0.1 mg/mL, more preferably 0.2 mg/mL, more preferably 0.3 mg/mL, more preferably 0.4 mg/mL, more preferably 0.5 mg/mL, more preferably 0.7 mg/mL, more preferably 1 mg/mL, more preferably 2 mg/mL, more preferably 3 mg/mL, more preferably 4 mg/mL, more preferably 5 mg/mL, more preferably 10 mg/mL, more preferably 20 mg/mL, even more preferably 30 mg/mL, still more preferably 40 mg/mL, yet still more preferably 50 mg/mL, more preferably 55 mg/mL, more preferably 75 mg/mL, more preferably 85 mg/mL, more preferably 100 mg/mL, more preferably 200 mg/mL, more preferably 300 mg/mL, more preferably 500 mg/mL and most preferably 1000 mg/mL.

In one embodiment, the salt is made with L-Lactic Acid and Semapimod.

In another embodiment, the salt is Semapimod with mesylate anion.

One embodiment of the present invention relates to pharmaceutical compositions comprising one or more pharmaceutically acceptable salts and one or more a pharmaceutically acceptable carrier, excipient, adjuvant and/or diluent. Other embodiments relate to methods of making and using the salts, for example wherein the salt is used to assay or test the guanylhydrazone compound or methods of use in which the guanylhydrazone compound is the active principle in a known therapy using that active principle.

The salts may be suitably prepared according to known methods, for example, by contacting the free base form of the guanylhydrazone containing compound with a sufficient amount of the desired acid to produce a salt in the conventional manner.

The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

The salts cam be administered in combination with one or more substantially nontoxic pharmaceutically acceptable carriers, excipients, adjuvants or diluents. The compositions of the present invention may be prepared in any conventional solid or liquid carrier or diluent and optionally any conventional pharmaceutically-made adjuvant at suitable dosage level in a known way. The preferred preparations are in administrable form which is suitable for oral application. These administrable forms, for example, include pills, tablets, film tablets, coated tablets, capsules, powders and deposits.

Forms other than orally administrable forms are also possible. The compounds of the present invention and/or pharmaceutical preparations containing said compounds may be administered by any appropriate means, including but not limited to injection (intravenous, intraperitoneal, intramuscular, subcutaneous) by absorption through epithelial or mucocutaneous linings (oral mucosa, rectal and vaginal epithelial linings, nasopharyngeal mucosa, intestinal mucosa); orally, rectally, transdermally, topically, intradermally, intragastrally, intracutanly, intravaginally, intravasally, intranasally, intrabuccally, percutanly, sublingually, or any other means available within the pharmaceutical arts.

The pharmaceutically acceptable carrier may be suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the salt may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent by weight of the inventive compound, salt thereof, or a mixture of compound and salt, which range includes all values and subranges therebetween, including 10, 15, 20, 25, 30, 35, 40, 45, 50, 55, 60, 65, 70, 75, 80, 85, and 90% by weight.

Suitable binders include starch, gelatin, natural sugars, corn sweeteners, natural and synthetic gums such as acacia, sodium alginate, carboxymethyl-cellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compounds or compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of various disintegration rates or controlled release polymeric matrices impregnated with the active components and shaped in tablet form or capsules containing such impregnated or encapsulated porous polymeric matrices.

Liquid form preparations include solutions, suspensions and emulsions. Nonlimiting examples include water, ethanol, ethanolic, water-ethanol or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the present invention may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refers to the active ingredients dispersed or solubilized in a hydrophillic semi-solid matrix.

Powders for constitution refers to powder blends containing the active ingredients and suitable diluents which can be suspended in water or juices.

Suitable diluents are substances that usually make up the major portion of the composition or dosage form.

Suitable diluents include sugars such as lactose, sucrose, mannitol and sorbitol, starches derived from wheat, corn rice and potato, and celluloses such as microcrystalline cellulose. The amount of diluent in the composition can range from about 5 to about 95% by weight of the total composition, preferably from about 25 to about 75%, more preferably from about 30 to about 60% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 2 to about 20% by weight of the composition, more preferably from about 5 to about 10% by weight.

Binders characterize substances that bind or "glue" powders together and make them cohesive by forming granules, thus serving as the "adhesive" in the formulation. Binders add cohesive strength already available in the diluent or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents are materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Other techniques for formulation and administration may be found in "Remington's Pharmaceutical Sciences" Mack Publishing Co., Easton Pa., the entire contents of which are hereby incorporated by reference. A suitable composition comprising at least one compound of the invention may be a solution of the compound in a suitable liquid pharmaceutical carrier or any other formulation such as tablets, pills, film tablets, coated tablets, dragees, capsules, powders and deposits, gels, syrups, slurries, suspensions, emulsions, and the like.

The term "treating" as used herein refers to reversing, alleviating, inhibiting the progress of, or preventing the disorder or condition to which the term applies, or one or more symptoms of the disorder or condition. The term "treatment" as used herein refers to the act of treating as the term is defined above.

The compound of the present invention may exist in any convenient crystalline, semicrystalline, or amorphous form. These may be achieved via typical crystallization routes including vacuum crystallization or spray drying. Depending on the solubility desired, the amorphous form obtained by, e.g., spray-drying may be preferred. The spray drying may be carried out from aqueous, ethanolic, organic, or mixed aqueous ethanolic solutions of the salt or a mixture of the salt and the free base compound. The compound and/or salt may exist in a form comprising one or more waters of hydration.

The guanylhydrazone compound is suitably administered in the form of a salt of a pharmaceutically acceptable acid. The pharmaceutically acceptable salt desirably satisfies one or more of the following physiochemical criteria: (1) good solubility; (2) good stability; (3) non-hydroscopicity; (4) processability for oral, parenteral, or topical formulations, etc. A range of pharmaceutically acceptable guanylhydrazone salts have been made and evaluated using these criteria.

The present salts desirably have good aqueous solubility and good bioavailability. Usually a solubility of greater than 1 mg/mL at pH 1-7.5 is sought although higher solubilities are required to formulate injections. In addition, salts which provide solutions having a pH close to that of blood (7.4) are preferred because they are readily biocompatible and can easily be buffered to the required pH range without altering their solubility. The L-lactate salt of Semapimod exhibits very good solubility.

Good stability in the solid state is desirable for tablets and capsules, while good stability in solution is required for an aqueous injection. In the case of tablets the vehicle can be comprised of, for instance, microcrystalline cellulose in 50:50 combination with anhydrous dibasic calcium phosphate. In the case of capsules the vehicles can be comprised of, for instance, mannitol in 4:1 combination with dried maize starch. In order to provide stable formulations it is desirable to have a non-hygroscopic salt. In the solid state where drug content is high, absorbed films of moisture can act as a vector for hydrolysis and chemical breakdown. It is the hygroscopic nature of a drug or its salt which contributes to the free moisture which is normally responsible for instability.

The present salts are desirably easily processed, i.e. they have good compression properties and also the ability not to stick or adhere to the tablet making machinery. For high dose formulations, good compressibility is desirable in terms of making elegant tablets. With lower dose tablets the need for good compressibility can be eliminated to a certain extent by the use of suitable diluting excipients called compression aids. Microcrystalline cellulose is a commonly used compression aid.

EXAMPLES

In order that the present invention be more readily understood, reference is now made to the following Examples, which are not intended to be limiting unless otherwise indicated.

Example 1

Procedure for Semapimod Free Base Preparation

An AG1-X8 resin from Bio-Rad (20-50 mesh, hydroxide form, 20 g) was swished in 100 mL of 1 N NaOH solution at room temp. for about 5 minutes, and was filtered. The resin was then rinsed with 100 mL of $H_2O$, followed by 200 mL of MeOH. The resin was then added to 50 mL of a MeOH solution containing 2 g of the Semapimod-4 HCl salt. The mixture was then stirred at room temp. for 60 min, and then filtered.

The resin was rinsed with about 50 mL of MeOH. The combined filtrate was concentrated under reduced pressure to afford 1.72 g of a light yellow solid. HPLC analysis of the product showed 98.9% purity. The product prepared from the same procedure was subjected to elemental analysis, and the results showed a closer match to Semapimod-4 $H_2O$. $^1H$ NMR of the product showed the same pattern of spectrum as the starting material, but with the signals from the methyl group and the aromatic hydrogen slightly shifted up-field. Recovery from this process was usually more than 95%.

Example 2

Solubility of Semapimod-2 HCl/4 $H_2O$

The product isolated as Semapimod-2 HCl/4 H2O was added to ca. 2 mL of solvents ($H_2O$, 5% Dextrose solution, PBS, and 0.9% NaCl solution), and was sonicated at room temperature until the solid suspended in the solution. The mixture was passed through a Nylon syringe filter, and then 0.5 mL of the filtrate was diluted with MeOH before injection into the HPLC. The concentration of Semapimod-2 HCl/4 $H_2O$ in the filtrate was calculated by comparing the results with a standard solution prepared from Semapimod-4 HCl/4 $H_2O$. For reference purpose, the solubility of Semapimod-4 HCl/4 $H_2O$ was determined according to the previous procedure.

The solubility of Semapimod-2 HCl/4 $H_2O$ was examined and is listed below:
$H_2O$: ca. 9.54 mg/mL
5% Dextrose: 13.44 mg/mL
PBS: 0
0.9% NaCl soln: 0
The solubility of Semapimod-4 HCl/4 $H_2O$
$H_2O$: 14.15 mg/mL Example 3

Preparation of Semapimod (CNI-1493) Salts

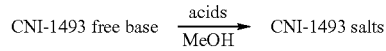

The following Semapimod salts were prepared according to the procedure described above. The results are summarized in the following Table:

TABLE I

| Salts | Filtration | Form |
| --- | --- | --- |
| acetate | easy | white solid |
| L-glutamate | medium | white solid |
| L-lactate | easy | white solid |
| mesylate | medium[1] | white solid |
| sulfate | easy | white solid |

[1]Product was tacky and adhered to the reaction vessel.

The Semapimod sulfate precipitated out of the solution as a white solid, and the isolated product was not soluble in DMSO-d6, methanol-d4, or D2.

Example 4

Solubility Testing

The Semapimod salts mentioned in the above table were subjected to solubility tests using the same procedure outlined above. The results were compared to a standard solution prepared from Semapimod-4 HCl/4 $H_2O$ to determine the concentration of the salts in either $H_2O$ or 5% dextrose solution. The results are listed in the following table:

TABLE II

| Salts | Solubility in $H_2O$[1], (mg/mL)[2] | Solubility in 5% dextrose solution, (mg/mL)[2] |
| --- | --- | --- |
| acetate | 43.3 | 18.1 |
| L-glutamate | ≧51.8 | ≧42.7 |
| L-lactate | ≧59.2 | ≧49.9 |
| mesylate | 35.4 | ≧46.4 |
| sulfate | 0 | 0 |

[1]$H_2O$ was from Pharmco, HPLC grade, and was used without further modification.
[2]The molecular weight of each salt was assumed 900 to get the approximate readings in mg/mL.

For Semapimod glutamate and lactate, both salts appeared to be soluble freely in $H_2O$ and 5% dextrose solution. To conserve the products, solutions less than saturation used in the solubility test.

It will be recognized by those skilled in the art that changes can be made to the embodiments of the invention without departing from the broad inventive concepts thereof. It is understood, therefore, that this invention is not limited to the particular embodiments disclosed, but is intended to cover all modifications which are within the spirit and scope of the invention.

The invention claimed is:

1. A pharmaceutically acceptable salt, comprising one or more compounds having the formula:

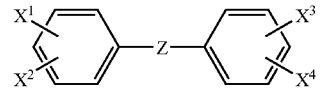

wherein $X^1$ and $X^2$ each independently represent GhyCH— or GhyCCH$_3$—, and $X^3$ and $X^4$ are each H;
wherein Z is -$(A^1)_a$-$(CR^2R^3)_x$-$(A^2)_b$-;
wherein a is selected from the group consisting of 0, 1, 2, 3, 4, 5, 6, 7, 8, and 9;
wherein b is selected from the group consisting of 0, 1, 2, 3, 4, 5, 6, 7, 8, and 9;
wherein x is selected from the group consisting of 0, 1, 2, 3, 4, 5, 6, 7, 8, and 9;
wherein $A^1$ and $A^2$ are each independently selected from the group consisting of —NR$^8$(CO)NR$^9$—, —(CO)NR$^8$—, —NR$^8$(CO)—, —NR$^8$—, —O—, —S—, —S(=O)—, —SO$_2$—, —SO$_2$NR$^8$—, —NR$^8$SO$_2$—, and salts thereof;
wherein $R^2$ and $R^3$ are each independently selected from the group consisting of hydrogen, hydroxy, halo, bromo, chloro, iodo, fluoro, —N$_3$, —CN, —NC, —SH, —NO$_2$, —NH$_2$, (C$_1$-C$_{20}$)alkyl, phenyl, (C$_3$-C$_{20}$)cycloalkyl, (C$_1$-C$_{20}$)alkoxy, (C$_3$-C$_{25}$)heteroaryl, (C$_3$-C$_{25}$)heterocyclic, (C$_2$-C$_{20}$)alkenyl, (C$_3$-C$_{20}$)cycloalkenyl, (C$_2$-C$_{20}$)alkynyl, (C$_5$-C$_{20}$)cycloalkynyl, (C$_5$-C$_{25}$)aryl, perhalo(C$_1$-C$_{20}$)alkyl, (C$_1$-C$_{20}$)alkyl-O—, phenyl-O—, (C$_3$-C$_{20}$)cycloalkyl-O—, (C$_3$-C$_{25}$)heteroaryl-O—, (C$_3$-C$_{25}$)heterocyclic-O—, (C$_2$-C$_{20}$)alkenyl-O—, (C$_3$-C$_{20}$)cycloalkenyl-O—, (C$_2$-C$_{20}$)alkynyl-O—, (C$_5$-C$_{20}$)cycloalkynyl-O—, (C$_5$-C$_{25}$)aryl-O—, perhalo(C$_1$-C$_{20}$)alkyl-O—, (C$_1$-C$_{20}$)alkyl-S—, phenyl-S—, (C$_3$-C$_{20}$)cycloalkyl-S—, (C$_3$-C$_{25}$)heteroaryl-S—, (C$_3$-C$_{25}$)heterocyclic-S—, (C$_2$-C$_{20}$)alkenyl-S—, (C$_3$-C$_{20}$)cycloalkenyl-S—, (C$_2$-C$_{20}$)alkynyl-S—, (C$_5$-C$_{20}$)cycloalkynyl-S—, (C$_5$-C$_{25}$)aryl-S—, perhalo(C$_1$-C$_{20}$)alkyl-S—, (C$_1$-C$_{20}$)alkyl-SO$_2$—, phenyl-SO$_2$—, (C$_3$-C$_{20}$)cycloalkyl-SO$_2$—, (C$_1$-C$_{20}$)alkoxy-SO$_2$—, (C$_3$-C$_{25}$)heteroaryl-SO$_2$—, (C$_3$-C$_{25}$)heterocyclic-SO$_2$—, (C$_2$-C$_{20}$)alkenyl-SO$_2$—, (C$_3$-C$_{20}$)cycloalkenyl-SO$_2$—, (C$_2$-C$_{20}$)alkynyl-SO$_2$—, (C$_5$-C$_{20}$)cycloalkynyl-SO$_2$—, $(C_5-C_{25})$aryl-$SO_2$—, perhalo$(C_1-C_{20})$alkyl-$SO_2$—, $H_2N$—$SO_2$—, $(C_1-C_{20})$alkyl-NH—$SO_2$—, phenyl-NH—$SO_2$—, $(C_3-C_{20})$cycloalkyl-NH—$SO_2$—, $(C_1-C_{20})$alkoxy-NH—$SO_2$—, $(C_3-C_{25})$heteroaryl-NH—$SO_2$—, $(C_3-C_{25})$heterocyclic-NH—$SO_2$—, $(C_2-C_{20})$alkenyl-NH—$SO_2$—, $(C_3-C_{20})$cycloalkenyl-NH—$SO_2$—, $(C_2-C_{20})$alkynyl-NH—$SO_2$—, $(C_5-C_{20})$cycloalkynyl-NH—$SO_2$—, $(C_5-C_{25})$aryl-NH—$SO_2$—, perhalo$(C_1-C_{20})$alkyl-NH—$SO_2$—, $\{(C_1-C_{20})$alkyl$\}_2$N—$SO_2$—, $\{$phenyl$\}_2$N—$SO_2$—, $\{(C_3-C_{20})$cycloalkyl$\}_2$N—$SO_2$—, $\{(C_1-C_{20})$alkoxy$\}_2$N—$SO_2$—, $\{(C_3-C_{25})$heteroaryl$\}_2$N—$SO_2$—, $\{(C_3-C_{25})$heterocyclic$\}_2$N—$SO_2$—, $\{(C_2-C_{20})$alkenyl$\}_2$N—$SO_2$—, $\{(C_2-C_{20})$alkynyl$\}_2$N—$SO_2$—, $\{(C_5-C_{20})$cycloalkynyl$\}_2$N—$SO_2$—, $\{(C_5-C_{25})$aryl$\}_2$N—$SO_2$—, $\{$perhalo$(C_1-C_{20})$alkyl$\}_2$N—$SO_2$—, $(C_1-C_{20})$alkyl-$SO_2$—NH—, phenyl-$SO_2$—NH—, $(C_3-C_{20})$cycloalkyl-$SO_2$—NH—, $(C_1-C_{20})$alkoxy-$SO_2$—NH—, $(C_3-C_{25})$heteroaryl-$SO_2$—NH—, $(C_3-C_{25})$heterocyclic-$SO_2$—NH—, $(C_2-C_{20})$alkenyl-$SO_2$—NH—, $(C_3-C_{20})$cycloalkenyl-$SO_2$—NH—, $(C_2-C_{20})$alkynyl-$SO_2$—NH—, $(C_5-C_{20})$cycloalkynyl-$SO_2$—NH—, $(C_5-C_{25})$aryl-$SO_2$—NH—, perhalo$(C_1-C_{20})$alkyl-$SO_2$—NH—, $(C_1-C_{20})$alkyl-NH—, phenyl-NH—, $(C_3-C_{20})$cycloalkyl-NH—, $(C_1-C_{20})$alkoxy-NH—, $(C_3-C_{25})$heteroaryl-NH—, $(C_3-C_{25})$heterocyclic-NH—, $(C_2-C_{20})$alkenyl-NH—, $(C_3-C_{20})$cycloalkenyl-NH—, $(C_2-C_{20})$alkynyl-NH—, $(C_5-C_{20})$cycloalkynyl-NH—, $(C_5-C_{25})$aryl-NH—, perhalo$(C_1-C_{20})$alkyl-NH—, $\{(C_1-C_{20})$alkyl$\}_2$N—, $\{$phenyl$\}_2$N—, $\{(C_3-C_{20})$cycloalkyl$\}_2$N—, $\{(C_1-C_{20})$alkoxy$\}_2$N—, $\{(C_3-C_{25})$heteroaryl$\}_2$N—, $\{(C_3-C_{25})$heterocyclic$\}_2$N—, $\{(C_2-C_{20})$alkenyl$\}_2$N—, $\{(C_3-C_{20})$cycloalkenyl$\}_2$N—, $\{(C_2-C_{20})$alkynyl$\}_2$N—, $\{(C_5-C_{20})$cycloalkynyl$\}_2$N—, $\{(C_5-C_{25})$aryl$\}_2$N—, $\{$perhalo$(C_1-C_{20})$alkyl$\}_2$N—, $(C_1-C_{20})$alkyl-$(C=O)$—NH—, phenyl-$(C=O)$—NH—, $(C_3-C_{20})$cycloalkyl-$(C=O)$—NH—, $(C_1-C_{20})$alkoxy-$(C=O)$—NH—, $(C_3-C_{25})$heteroaryl-$(C=O)$—NH—, $(C_3-C_{25})$heterocyclic-$(C=O)$—NH—, $(C_2-C_{20})$alkenyl-$(C=O)$—NH—, $(C_3-C_{20})$cycloalkenyl-$(C=O)$—NH—, $(C_2-C_{20})$alkynyl-$(C=O)$—NH—, $(C_5-C_{20})$cycloalkynyl-$(C=O)$—NH—, $(C_5-C_{25})$aryl-$(C=O)$—NH—, perhalo$(C_1-C_{20})$alkyl-$(C=O)$—NH—, $(C_1-C_{20})$alkyl-$(C=O)$—$\{((C_1-C_{20})$alkyl$)$N$\}$—, phenyl-$(C=O)$—$\{((C_1-C_{20})$alkyl$)$N$\}$—, $(C_3-C_{20})$cycloalkyl-$(C=O)$—$\{((C_1-C_{20})$alkyl$)$N$\}$—, $(C_1-C_{20})$alkoxy-$(C=O)$—$\{((C_1-C_{20})$alkyl$)$N$\}$—, $(C_3-C_{25})$heteroaryl-$(C=O)$—$\{((C_1-C_{20})$alkyl$)$N$\}$—, $(C_3-C_{25})$heterocyclic-$(C=O)$—$\{((C_1-C_{20})$alkyl$)$N$\}$—, $(C_2-C_{20})$alkenyl-$(C=O)$-$\{((C_1-C_{20})$alkyl$)$N$\}$—, $(C_3-C_{20})$cycloalkenyl-$(C=O)$—$\{((C_1-C_{20})$alkyl$)$N$\}$—, $(C_2-C_{20})$alkynyl-$(C=O)$—$\{((C_1-C_{20})$alkyl$)$N$\}$—, $(C_5-C_{20})$cycloalkynyl-$(C=O)$—$\{((C_1-C_{20})$alkyl$)$N$\}$—, $(C_5-C_{25})$aryl-$(C=O)$—$\{((C_1-C_{20})$alkyl$)$N$\}$—, perhalo$(C_1-C_{20})$alkyl-$(C=O)$—$\{((C_1-C_{20})$alkyl$)$N$\}$—, phenyl-$(C=O)$—NH—, phenyl-$(C=O)$-$\{($phenyl$)$N$\}$—, $(C_1-C_{20})$alkyl-$(C=O)$-$\{($phenyl$)$N$\}$—, $(C_3-C_{20})$cycloalkyl-$(C=O)$-$\{($phenyl$)$N$\}$—, $(C_1-C_{20})$alkoxy-$(C=O)$-$\{($phenyl$)$N$\}$—, $(C_3-C_{25})$heteroaryl-$(C=O)$-$\{($phenyl$)$N$\}$—, $(C_3-C_{25})$heterocyclic-$(C=O)$-$\{($phenyl$)$N$\}$—, $(C_2-C_{20})$alkenyl-$(C=O)$-$\{($phenyl$)$N$\}$—, $(C_3-C_{20})$cycloalkenyl-$(C=O)$-$\{($phenyl$)$N$\}$—, $(C_2-C_{20})$alkynyl-$(C=O)$-$\{($phenyl$)$N$\}$—, $(C_5-C_{20})$cycloalkynyl-$(C=O)$-$\{($phenyl$)$N$\}$—, $(C_5-C_{25})$aryl-$(C=O)$-$\{($phenyl$)$N$\}$—, perhalo$(C_1-C_{20})$alkyl-$(C=O)$-$\{($phenyl$)$N$\}$—, $H_2N(C=O)$—, $(C_1-C_{20})$alkyl-NH—$(C=O)$—, phenyl-NH—$(C=O)$—, $(C_3-C_{20})$cycloalkyl-NH—$(C=O)$—, $(C_1-C_{20})$alkoxy-NH—$(C=O)$—, $(C_3-C_{25})$heteroaryl-NH—$(C=O)$—, $(C_3-C_{25})$heterocyclic-NH—$(C=O)$—, $(C_2-C_{20})$alkenyl-NH—$(C=O)$—, $(C_3-C_{20})$cycloalkenyl-NH—$(C=O)$—, $(C_2-C_{20})$alkynyl-NH—$(C=O)$—, $(C_5-C_{20})$cycloalkynyl-NH—$(C=O)$—, $(C_5-C_{25})$aryl-NH—$(C=O)$—, perhalo$(C_1-C_{20})$alkyl-NH—$(C=O)$—, $\{C_1-C_{20})$alkyl$\}_2$N—$(C=O)$—, $\{$phenyl$\}(C_1-C_{20})$alkyl$\}$N—$(C=O)$—, $\{(C_3-C_{20})$cycloalkyl$\}\{(C_1-C_{20})$alkyl$\}$N—$(C=O)$—, $\{(C_1-C_{20})$alkoxy$\}\{(C_1-C_{20})$alkyl$\}$N—$(C=O)$—, $\{(C_3-C_{25})$heteroaryl$\}\{(C_1-C_{20})$alkyl$\}$N—$(C=O)$—, $\{(C_3-C_{25})$heterocyclic$\}\{(C_1-C_{20})$alkyl$\}$N—$(C=O)$—, $\{(C_2-C_{20})$alkenyl$\}\{(C_1-C_{20})$alkyl$\}$N—$(C=O)$—, $\{(C_3-C_{20})$cycloalkenyl$\}\{(C_1-C_{20})$alkyl$\}$N—$(C=O)$—, $\{(C_2-C_{20})$alkynyl$\}\{(C_1-C_{20})$alkyl$\}$N—$(C=O)$—, $\{(C_5-C_{20})$cycloalkynyl$\}\{(C_1-C_{20})$alkyl$\}$N—$(C=O)$—, $\{(C_5-C_{25})$aryl$\}\{(C_1-C_{20})$alkyl$\}$N—$(C=O)$—, $\{$perhalo$(C_1-C_{20})$alkyl$\}\{(C_1-C_{20})$alkyl$\}$N—$(C=O)$—, $\{$phenyl$\}_2$N—$(C=O)$—, $\{(C_3-C_{20})$cycloalkyl$\}\{$phenyl$\}$N—$(C=O)$—, $\{(C_1-C_{20})$alkoxy$\}\{$phenyl$\}$N—$(C=O)$—, $\{(C_3-C_{25})$heteroaryl$\}\{$phenyl$\}$N—$(C=O)$—, $\{(C_3-C_{25})$heterocyclic$\}\{$phenyl$\}$N—$(C=O)$—, $\{(C_2-C_{20})$alkenyl$\}\{$phenyl$\}$N—$(C=O)$—, $\{(C_3-C_{20})$cycloalkenyl$\}\{$phenyl$\}$N—$(C=O)$—, $\{(C_2-C_{20})$alkynyl$\}\{$phenyl$\}$N—$(C=O)$—, $\{(C_5-C_{20})$cycloalkynyl$\}\{$phenyl$\}$N—$(C=O)$—, $\{(C_5-C_{25})$aryl$\}\{$phenyl$\}$N—$(C=O)$—, $\{$perhalo$(C_1-C_{20})$alkyl$\}\{$phenyl$\}$N—$(C=O)$—, HO—$(C=O)$—, $(C_1-C_{20})$alkyl-$(C=O)$—, $(C_3-C_{25})$heteroaryl-$(C=O)$—, $(C_3-C_{25})$heterocyclic-$(C=O)$—, $(C_2-C_{20})$alkenyl-$(C=O)$—, $(C_3-C_{20})$cycloalkenyl-$(C=O)$—, $(C_2-C_{20})$alkynyl-$(C=O)$—, $(C_5-C_{25})$aryl-$(C=O)$—, perhalo$(C_1-C_{20})$alkyl-$(C=O)$—, phenyl-$(C=O)$—, $(C_1-C_{20})$alkyl-O—$(C=O)$—, $(C_3-C_{25})$heteroaryl-O—$(C=O)$—, $(C_3-C_{25})$heterocyclic-O—$(C=O)$—, $(C_2-C_{20})$alkenyl-O—$(C=O)$—, $(C_3-C_{20})$cycloalkenyl-O—$(C=O)$—, $(C_2-C_{20})$alkynyl-O—$(C=O)$—, $(C_5-C_{25})$aryl-O—$(C=O)$—, perhalo$(C_1-C_{20})$alkyl-O—$(C=O)$—, phenyl-O—$(C=O)$—, $(C_1-C_{20})$alkyl-$(C=O)$—O—, $(C_3-C_{25})$heteroaryl-$(C=O)$—O—, $(C_3-C_{25})$heterocyclic-$(C=O)$—O—, $(C_2-C_{20})$alkenyl-$(C=O)$—O—, $(C_3-C_{20})$cycloalkenyl-$(C=O)$—O—, $(C_2-C_{20})$alkynyl-$(C=O)$—O—, $(C_5-C_{25})$aryl-$(C=O)$—O—, phenyl-$(C=O)$—O—, perhalo$(C_1-C_{20})$alkyl-$(C=O)$—O—, and salts thereof;

wherein each of the aforesaid $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, and $(C_5-C_{25})$aryl groups (for said $R^2$ and $R^3$ groups) may be optionally and independently substituted by one to four moieties selected from the group consisting of hydroxy, halo, bromo, chloro, iodo, fluoro, —$N_3$, —CN, —NC, —SH, —$NO_2$, —$NH_2$, $(C_1-C_{20})$alkyl, phenyl, $(C_3-C_{20})$cycloalkyl, $(C_1-C_{20})$alkoxy, $(C_3-C_{25})$heteroaryl, $(C_3-C_{25})$heterocyclic, $(C_2-C_{20})$alkenyl, $(C_3-C_{20})$cycloalkenyl, $(C_2-C_{20})$alkynyl, $(C_5-C_{20})$cycloalkynyl, $(C_5-C_{25})$aryl, perhalo$(C_1-C_{20})$alkyl, $(C_1-C_{20})$alkyl-O—, phenyl-O—, $(C_3-C_{20})$cycloalkyl-O—, $(C_3-C_{25})$heteroaryl-O—, $(C_3-C_{25})$heterocyclic-O—, $(C_2-C_{20})$alkenyl-O—, $(C_3-C_{20})$cycloalkenyl-O—, $(C_2-C_{20})$alkynyl-O—, $(C_5-C_{20})$cycloalkynyl-O—, $(C_5-C_{25})$aryl-O—, perhalo$(C_1-C_{20})$alkyl-O—, $(C_1-C_{20})$alkyl-S—, phenyl-S—, $(C_3-C_{20})$cycloalkyl-S—, $(C_3-C_{25})$heteroaryl-S—, $(C_3-C_{25})$heterocyclic-S—, $(C_2-C_{20})$alkenyl-S—, $(C_3-C_{20})$cycloalkenyl-S—, $(C_2-C_{20})$alkynyl-S—, $(C_5-C_{20})$ cycloalkynyl-S—, $(C_5-C_{25})$aryl-S—, perhalo$(C_1-C_{20})$alkyl-S—, $(C_1-C_{20})$alkyl-SO$_2$—, phenyl-SO$_2$—, $(C_3-C_{20})$cycloalkyl-SO$_2$—, $(C_1-C_{20})$alkoxy-SO$_2$—, $(C_3-C_{25})$heteroaryl-SO$_2$—, $(C_3-C_{25})$heterocyclic-SO$_2$—, $(C_2-C_{20})$alkenyl-SO$_2$—, $(C_3-C_{20})$cycloalkenyl-SO$_2$—, $(C_2-C_{20})$alkynyl-SO$_2$—, $(C_5-C_{20})$cycloalkynyl-SO$_2$—, $(C_5-C_{25})$aryl-SO$_2$—, perhalo$(C_1-C_{20})$alkyl-SO$_2$—, H$_2$N—SO$_2$—, $(C_1-C_{20})$alkyl-NH—SO$_2$—, phenyl-NH—SO$_2$—, $(C_3-C_{20})$cycloalkyl-NH—SO$_2$—, $(C_1-C_{20})$alkoxy-NH—SO$_2$—, $(C_3-C_{25})$heteroaryl-NH—SO$_2$—, $(C_3-C_{25})$heterocyclic-NH—SO$_2$—, $(C_2-C_{20})$alkenyl-NH—SO$_2$—, $(C_3-C_{20})$cycloalkenyl-NH—SO$_2$—, $(C_2-C_{20})$alkynyl-NH—SO$_2$—, $(C_5-C_{20})$cycloalkynyl-NH—SO$_2$—, $(C_5-C_{25})$aryl-NH—SO$_2$—, perhalo$(C_1-C_{20})$alkyl-NH—SO$_2$—, $\{(C_1-C_{20})$alkyl$\}_2$N—SO$_2$—, $\{$phenyl$\}_2$N—SO$_2$—, $\{(C_3-C_{20})$cycloalkyl$\}_2$N—SO$_2$—, $\{(C_1-C_{20})$alkoxy$\}_2$N—SO$_2$—, $\{(C_3-C_{25})$heteroaryl$\}_2$N—SO$_2$—, $\{(C_3-C_{25})$heterocyclic$\}_2$N—SO$_2$—, $\{(C_2-C_{20})$alkenyl$\}_2$N—SO$_2$—, $\{(C_2-C_{20})$alkynyl$\}_2$N—SO$_2$—, $\{(C_5-C_{20})$cycloalkynyl$\}_2$N—SO$_2$—, $\{(C_5-C_{25})$aryl$\}_2$N—SO$_2$—, $\{$perhalo$(C_1-C_{20})$alkyl$\}_2$N—SO$_2$—, $(C_1-C_{20})$alkyl-SO$_2$—NH—, phenyl-SO$_2$—NH—, $(C_3-C_{20})$cycloalkyl-SO$_2$—NH—, $(C_1-C_{20})$alkoxy-SO$_2$—NH—, $(C_3-C_{25})$heteroaryl-SO$_2$—NH—, $(C_3-C_{25})$heterocyclic-SO$_2$—NH—, $(C_2-C_{20})$alkenyl-SO$_2$—NH—, $(C_3-C_{20})$cycloalkenyl-SO$_2$—NH—, $(C_2-C_{20})$alkynyl-SO$_2$—NH—, $(C_5-C_{20})$cycloalkynyl-SO$_2$—NH—, $(C_5-C_{25})$aryl-SO$_2$—NH—, perhalo$(C_1-C_{20})$alkyl-SO$_2$—NH—, $(C_1-C_{20})$alkyl-NH—, phenyl-NH—, $(C_3-C_{20})$cycloalkyl-NH—, $(C_1-C_{20})$alkoxy-NH—, $(C_3-C_{25})$heteroaryl-NH—, $(C_3-C_{25})$heterocyclic-NH—, $(C_2-C_{20})$alkenyl-NH—, $(C_3-C_{20})$cycloalkenyl-NH—, $(C_2-C_{20})$alkynyl-NH—, $(C_5-C_{20})$cycloalkynyl-NH—, $(C_5-C_{25})$aryl-NH—, perhalo$(C_1-C_{20})$alkyl-NH—, $\{(C_1-C_{20})$alkyl$\}_2$N—, $\{$phenyl$\}_2$N—, $\{(C_3-C_{20})$cycloalkyl$\}_2$N—, $\{(C_1-C_{20})$alkoxy$\}_2$N—, $\{(C_3-C_{25})$heteroaryl$\}_2$N—, $\{(C_3-C_{25})$heterocyclic$\}_2$N—, $\{(C_2-C_{20})$alkenyl$\}_2$N—, $\{(C_3-C_{20})$cycloalkenyl$\}_2$N—, $\{(C_2-C_{20})$alkynyl$\}_2$N—, $\{(C_5-C_{20})$cycloalkynyl$\}_2$N—, $\{(C_5-C_{25})$aryl$\}_2$N—, $\{$perhalo$(C_1-C_{20})$alkyl$\}_2$N—, $(C_1-C_{20})$alkyl-(C=O)—NH—, phenyl-(C=O)—NH—, $(C_3-C_{20})$cycloalkyl-(C=O)—NH—, $(C_1-C_{20})$alkoxy-(C=O)—NH—, $(C_3-C_{25})$heteroaryl-(C=O)—NH—, $(C_3-C_{25})$heterocyclic-(C=O)—NH—, $(C_2-C_{20})$alkenyl-(C=O)—NH—, $(C_3-C_{20})$cycloalkenyl-(C=O)—NH—, $(C_2-C_{20})$alkynyl-(C=O)—NH—, $(C_5-C_{20})$cycloalkynyl-(C=O)—NH—, $(C_5-C_{25})$aryl-(C=O)—NH—, perhalo$(C_1-C_{20})$alkyl-(C=O)—NH—, $(C_1-C_{20})$alkyl-(C=O)—$\{((C_1-C_{20})$alkyl)N$\}$—, phenyl-(C=O)—$\{((C_1-C_{20})$alkyl)N$\}$—, $(C_3-C_{20})$cycloalkyl-(C=O)—$\{((C_1-C_{20})$alkyl)N$\}$—, $(C_1-C_{20})$alkoxy-(C=O)—$\{((C_1-C_{20})$alkyl)N$\}$—, $(C_3-C_{25})$heteroaryl-(C=O)—$\{((C_1-C_{20})$alkyl)N$\}$—, $(C_3-C_{25})$heterocyclic-(C=O)—$\{((C_1-C_{20})$alkyl)N$\}$—, $(C_2-C_{20})$alkenyl-(C=O)—$\{((C_1-C_{20})$alkyl)N$\}$—, $(C_3-C_{20})$cycloalkenyl-(C=O)—$\{((C_1-C_{20})$alkyl)N$\}$—, $(C_2-C_{20})$alkynyl-(C=O)—$\{((C_1-C_{20})$alkyl)N$\}$—, $(C_5-C_{20})$cycloalkynyl-(C=O)—$\{((C_1-C_{20})$alkyl)N$\}$—, $(C_5-C_{25})$aryl-(C=O)—$\{((C_1-C_{20})$alkyl)N$\}$—, perhalo$(C_1-C_{20})$alkyl-(C=O)—$\{((C_1-C_{20})$alkyl)N$\}$—, phenyl-(C=O)—NH—, phenyl-(C=O)-$\{$(phenyl)N$\}$—, $(C_1-C_{20})$alkyl-(C=O)-$\{$(phenyl)N$\}$—, $(C_3-C_{20})$cycloalkyl-(C=O)-$\{$(phenyl)N$\}$—, $(C_1-C_{20})$alkoxy-(C=O)-$\{$(phenyl)N$\}$—, $(C_3-C_{25})$heteroaryl-(C=O)-$\{$(phenyl)N$\}$—, $(C_3-C_{25})$heterocyclic-(C=O)-$\{$(phenyl)N$\}$—, $(C_2-C_{20})$alkenyl-(C=O)-$\{$(phenyl)N$\}$—, $(C_3-C_{20})$cycloalkenyl-(C=O)-$\{$(phenyl)N$\}$—, $(C_2-C_{20})$alkynyl-(C=O)-$\{$(phenyl)N$\}$—, $(C_5-C_{20})$cycloalkynyl-(C=O)-$\{$(phenyl)N$\}$—, $(C_5-C_{25})$aryl-(C=O)-$\{$(phenyl)N$\}$—, perhalo$(C_1-C_{20})$alkyl-(C=O)-$\{$(phenyl)N$\}$—, H$_2$N(C=O)—, $(C_1-C_{20})$alkyl-NH—(C=O)—, phenyl-NH—(C=O)—, $(C_3-C_{20})$cycloalkyl-NH—(C=O)—, $(C_1-C_{20})$alkoxy-NH—(C=O)—, $(C_3-C_{25})$heteroaryl-NH—(C=O)—, $(C_3-C_{25})$heterocyclic-NH—(C=O)—, $(C_2-C_{20})$alkenyl-NH—(C=O)—, $(C_3-C_{20})$cycloalkenyl-NH—(C=O)—, $(C_2-C_{20})$alkynyl-NH—(C=O)—, $(C_5-C_{20})$cycloalkynyl-NH—(C=O)—, $(C_5-C_{25})$aryl-NH—(C=O)—, perhalo$(C_1-C_{20})$alkyl-NH—(C=O)—, $\{C_1-C_{20})$alkyl$\}_2$N—(C=O)—, $\{$phenyl$\}\{(C_1-C_{20})$alkyl$\}$N—(C=O)—, $\{(C_3-C_{20})$cycloalkyl$\}\{(C_1-C_{20})$alkyl$\}$N—(C=O)—, $\{(C_1-C_{20})$alkoxy$\}\{(C_1-C_{20})$alkyl$\}$N—(C=O)—, $\{(C_3-C_{25})$heteroaryl$\}\{(C_1-C_{20})$alkyl$\}$N—(C=O)—, $\{(C_3-C_{25})$heterocyclic$\}\{(C_1-C_{20})$alkyl$\}$N—(C=O)—, $\{(C_2-C_{20})$alkenyl$\}\{(C_1-C_{20})$alkyl$\}$N—(C=O)—, $\{(C_3-C_{20})$cycloalkenyl$\}\{(C_1-C_{20})$alkyl$\}$N—(C=O)—, $\{(C_2-C_{20})$alkynyl$\}\{(C_1-C_{20})$alkyl$\}$N—(C=O)—, $\{(C_5-C_{20})$cycloalkynyl$\}\{(C_1-C_{20})$alkyl$\}$N—(C=O)—, $\{(C_5-C_{25})$aryl$\}\{(C_1-C_{20})$alkyl$\}$N—(C=O)—, $\{$perhalo$(C_1-C_{20})$alkyl$\}\{(C_1-C_{20})$alkyl$\}$N—(C=O)—, $\{$phenyl$\}_2$N—(C=O)—, $\{(C_3-C_{20})$cycloalkyl$\}\{$phenyl$\}$N—(C=O)—, $\{(C_1-C_{20})$alkoxy$\}\{$phenyl$\}$N—(C=O)—, $\{(C_3-C_{25})$heteroaryl$\}\{$phenyl$\}$N—(C=O)—, $\{(C_3-C_{25})$heterocyclic$\}\{$phenyl$\}$N—(C=O)—, $\{(C_2-C_{20})$alkenyl$\}\{$phenyl$\}$N—(C=O)—, $\{(C_2-C_{20})$cycloalkenyl$\}\{$phenyl$\}$N—(C=O)—, $\{(C_2-C_{20})$alkynyl$\}\{$phenyl$\}$N—(C=O)—, $\{(C_5-C_{20})$cycloalkynyl$\}\{$phenyl$\}$N—(C=O)—, $\{(C_5-C_{25})$aryl$\}\{$phenyl$\}$N—(C=O)—, $\{$perhalo$(C_1-C_{20})$alkyl$\}\{$phenyl$\}$N—(C=O)—, HO—(C=O)—, $(C_1-C_{20})$alkyl-(C=O)—, $(C_3-C_{25})$heteroaryl-(C=O)—, $(C_3-C_{25})$heterocyclic-(C=O)—, $(C_2-C_{20})$alkenyl-(C=O)—, $(C_3-C_{20})$cycloalkenyl-(C=O)—, $(C_2-C_{20})$alkynyl-(C=O)—, $(C_5-C_{25})$aryl-(C=O)—, perhalo$(C_1-C_{20})$alkyl-(C=O)—, phenyl-(C=O)—, $(C_1-C_{20})$alkyl-O—(C=O)—, $(C_3-C_{25})$heteroaryl-O—(C=O)—, $(C_3-C_{25})$heterocyclic-O—(C=O)—, $(C_2-C_{20})$alkenyl-O—(C=O)—, $(C_3-C_{20})$cycloalkenyl-O—(C=O)—, $(C_2-C_{20})$alkynyl-O—(C=O)—, $(C_5-C_{25})$aryl-O—(C=O)—, perhalo$(C_1-C_{20})$alkyl-O—(C=O)—, phenyl-O—(C=O)—, $(C_1-C_{20})$alkyl-(C=O)—O—, $(C_3-C_{25})$heteroaryl-(C=O)—O—, $(C_3-C_{25})$heterocyclic-(C=O)—O—, $(C_2-C_{20})$alkenyl-(C=O)—O—, $(C_3-C_{20})$cycloalkenyl-(C=O)—O—, $(C_2-C_{20})$alkynyl-(C=O)—O—, $(C_5-C_{25})$aryl-(C=O)—O—, phenyl-(C=O)—O—, perhalo$(C_1-C_{20})$alkyl-(C=O)—O—, and salts thereof;

and wherein two independently chosen $R^2$ and $R^3$ alkyl-containing groups may be taken together with any atom to which they are attached to form a three to forty membered cyclic, heterocyclic or heteroaryl ring;

as a salt of at least one pharmaceutically acceptable acid selected from the group consisting of compounds having the following formulas:

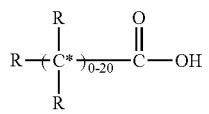

I

-continued

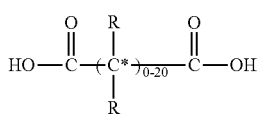

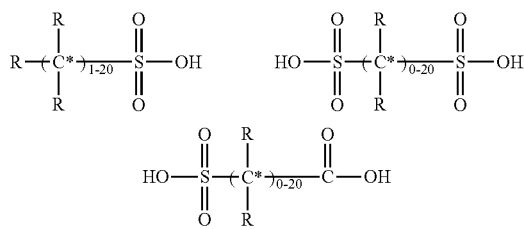

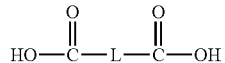

wherein each C* independently represents a potentially chiral carbon that can be in either the D or L enantiomeric configuration;

wherein each R is independently unsubstituted or substituted and selected from the group consisting of Y—, Y—O—, Y—S—, Y—SO$_2$—, (Y)$_2$—N—SO$_2$—, Y—(C=O)—, Y—(C=O)—O—, YO—(C=O)—, (Y)$_2$—N—, Y—(C=O)—(Y—N)—, (Y—(C=O))$_2$—N—, Y—(SO$_2$)—(Y—N)—, or (Y—(SO$_2$))$_2$—N—; each Y being independently selected from the group consisting of hydrogen, carboxyl, halo, hydroxyl, thiol, nitro, amine, NC—, (C$_1$-C$_6$)alkyl, (C$_3$-C$_6$)cycloalkyl, (C$_2$-C$_6$)alkenyl, (C$_3$-C$_6$)cycloalkenyl, (C$_2$-C$_6$)alkynyl, (C$_3$-C$_6$)cycloalkynyl, (C$_1$-C$_6$)alkoxy, (C$_5$-C$_7$)aryl, (C$_3$-C$_5$)heteroaryl, and (C$_3$-C$_5$)heterocyclic; wherein each of the aforesaid (C$_1$-C$_6$)alkyl, (C$_3$-C$_6$)cycloalkyl, (C$_2$-C$_6$)alkenyl, (C$_3$-C$_6$)cycloalkenyl, (C$_2$-C$_6$)alkynyl, (C$_3$-C$_6$)cycloalkynyl, (C$_1$-C$_6$)alkoxy, (C$_5$-C$_7$)aryl, (C$_3$-C$_5$) heteroaryl, and (C$_3$-C$_5$)heterocyclic substituents may be substituted or unsubstituted;

wherein two independently chosen Y alkyl-containing groups may be taken together with any nitrogen atom to which they are attached to form a three to twelve membered cyclic, heterocyclic or heteroaryl ring;

and wherein in the compound having the formula VII, L is a diradical moiety selected from the group consisting of (C$_1$-C$_{20}$)alkyl, (C$_3$-C$_{20}$)cycloalkyl, (C$_2$-C$_{20}$)alkenyl, (C$_3$-C$_{20}$)cycloalkenyl, (C$_2$-C$_{20}$)alkynyl, (C$_3$-C$_{20}$)cycloalkynyl, (C$_1$-C$_{20}$)alkoxy/thiol, (C$_3$-C$_{20}$)aryl, (C$_3$-C$_{15}$)heteroaryl, (C$_3$-C$_{15}$)heterocyclic and (C$_3$-C$_{20}$)cycloalkyl; wherein each of the aforesaid (C$_1$-C$_{20}$)alkyl, (C$_3$-C$_{20}$)cycloalkyl, (C$_2$-C$_{20}$)alkenyl, (C$_3$-C$_{20}$)cycloalkenyl, (C$_2$-C$_{20}$)alkynyl, (C$_3$-C$_{20}$)cycloalkynyl, (C$_1$-C$_{20}$)alkoxy/thiol, (C$_3$-C$_{20}$)aryl, (C$_3$-C$_{15}$)heteroaryl, (C$_3$-C$_{15}$)heterocyclic and (C$_3$-C$_{20}$)cycloalkyl diradical moieties may be substituted or unsubstituted.

2. The salt of claim 1, wherein the pharmaceutically acceptable acid has the following formula:

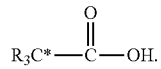

3. The salt of claim 1, wherein the pharmaceutically acceptable acid has the following formula:

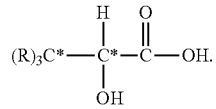

4. The salt of claim 1, wherein the pharmaceutically acceptable acid has the following formula:

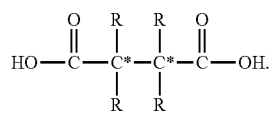

5. The salt of claim 1, wherein the pharmaceutically acceptable acid has the following formula:

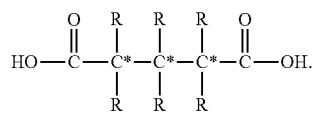

6. The salt of claim 1, wherein the pharmaceutically acceptable acid has the following formula:

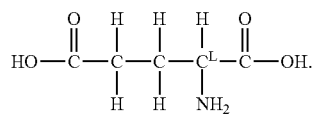

L-Glutamic Acid

7. The salt of claim 1, wherein the pharmaceutically acceptable acid has one of the following formulas:

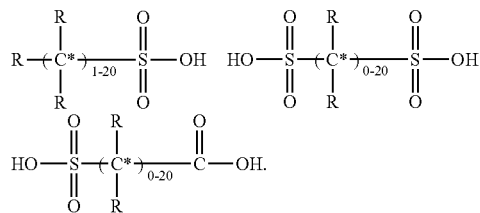

8. The salt of claim 1, wherein the pharmaceutically acceptable acid has the following formula:

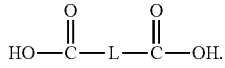 VII

9. A pharmaceutically acceptable composition, comprising the salt of claim 1 in contact with at least one pharmaceutically acceptable carrier.

10. The pharmaceutically acceptable salt of claim 1, wherein the pharmaceutically acceptable acid has the following formula:

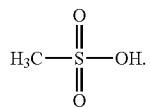

11. The pharmaceutically acceptable salt of claim 1, wherein the pharmaceutically acceptable acid has the following formula:

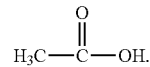

12. A method for making the salt of claim 1, comprising contacting said compound with said acid to form the salt.

13. A method for making the composition of claim 9, comprising contacting the salt and the pharmaceutically acceptable carrier, to form the composition.

14. The salt of claim 1, wherein $A^1$ and $A^2$ are each independently selected from the group consisting of $-NR^8-$, $-S-$, $-S(=O)-$, $-SO_2-$, $-SO_2NR^8-$, $-NR^8SO_2-$, and salts thereof.

* * * * *